(12) United States Patent
Aram et al.

(10) Patent No.: US 9,561,039 B2
(45) Date of Patent: Feb. 7, 2017

(54) CUSTOMIZED PATIENT-SPECIFIC ORTHOPAEDIC PIN GUIDES

(71) Applicant: DePuy Synthes Products, Inc., Raynham, MA (US)

(72) Inventors: Luke J. Aram, Warsaw, IN (US); Michael C. Jones, Warsaw, IN (US); James M. Rhodes, Warsaw, IN (US); Sonja R. Fussle, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/817,522

(22) Filed: Aug. 4, 2015

(65) Prior Publication Data

US 2015/0335339 A1 Nov. 26, 2015

Related U.S. Application Data

(60) Division of application No. 14/155,656, filed on Jan. 15, 2014, now Pat. No. 9,095,355, which is a continuation of application No. 13/173,880, filed on Jun. 30, 2011, now Pat. No. 8,641,721.

(51) Int. Cl.
*A61B 17/17* (2006.01)
*A61B 17/16* (2006.01)
*A61B 17/15* (2006.01)
*A61B 17/56* (2006.01)

(52) U.S. Cl.
CPC ....... *A61B 17/1721* (2013.01); *A61B 17/1675* (2013.01); *A61B 17/1764* (2013.01); *A61B 17/157* (2013.01); *A61B 2017/568* (2013.01)

(58) Field of Classification Search
CPC ..... A61B 17/17; A61B 17/16; A61B 17/1675; A61B 17/1764

USPC .......................................................... 606/88
See application file for complete search history.

(56) References Cited

U.S. PATENT DOCUMENTS

| | | |
|---|---|---|
| 3,298,410 A | 1/1967 | Noboru |
| 3,816,855 A | 6/1974 | Saleh |
| 3,901,298 A | 8/1975 | Eby |
| 3,965,950 A | 6/1976 | MacDonald |
| 4,055,862 A | 11/1977 | Farling |
| 4,140,161 A | 2/1979 | Russo et al. |
| 4,197,886 A | 4/1980 | MacDonald |
| 4,436,684 A | 3/1984 | White |
| 4,719,907 A | 1/1988 | Banko et al. |
| 4,721,104 A | 1/1988 | Kaufman et al. |
| 4,759,350 A | 7/1988 | Dunn et al. |

(Continued)

FOREIGN PATENT DOCUMENTS

| | | |
|---|---|---|
| DE | 3339259 C1 | 3/1985 |
| DE | 3925488 A1 | 2/1990 |

(Continued)

OTHER PUBLICATIONS

Berry, Seedhom, et al., "Personalised image-based templates for intra-operative guidance," Proceedings of the Institution of Mechanical Engineers, Part H: Journal of Engineering in Medicine, 111-118, 2005.

(Continued)

*Primary Examiner* — Christopher Beccia
(74) *Attorney, Agent, or Firm* — Barnes & Thornburg LLP

(57) ABSTRACT

Customized patient-specific orthopedic surgical instruments are disclosed. Methods for fabricating and using such instruments are also disclosed.

6 Claims, 15 Drawing Sheets

(56) References Cited

U.S. PATENT DOCUMENTS

| | | |
|---|---|---|
| 4,787,383 A | 11/1988 | Kenna |
| 4,834,080 A | 5/1989 | Brown |
| 4,841,975 A | 6/1989 | Woolson |
| 4,860,735 A | 8/1989 | Davey et al. |
| 5,053,037 A | 10/1991 | Lackey |
| 5,067,964 A | 11/1991 | Richmond et al. |
| 5,122,144 A | 6/1992 | Bert et al. |
| 5,129,908 A | 7/1992 | Petersen |
| 5,133,660 A | 7/1992 | Fenick |
| 5,186,174 A | 2/1993 | Schloendorff et al. |
| 5,258,032 A | 11/1993 | Bertin |
| 5,314,478 A | 5/1994 | Oka et al. |
| 5,314,482 A | 5/1994 | Goodfellow et al. |
| 5,320,529 A | 6/1994 | Pompa |
| 5,360,446 A | 11/1994 | Kennedy |
| 5,370,692 A | 12/1994 | Fink et al. |
| 5,417,694 A | 5/1995 | Marik et al. |
| 5,423,828 A | 6/1995 | Benson |
| 5,445,642 A | 8/1995 | McNulty et al. |
| 5,448,489 A | 9/1995 | Reuben |
| 5,458,645 A | 10/1995 | Bertin |
| 5,462,549 A | 10/1995 | Glock |
| 5,474,559 A | 12/1995 | Bertin et al. |
| 5,510,066 A | 4/1996 | Fink et al. |
| 5,514,139 A | 5/1996 | Goldstein et al. |
| 5,518,680 A | 5/1996 | Cima et al. |
| 5,520,695 A | 5/1996 | Luckman |
| 5,542,947 A | 8/1996 | Treacy |
| 5,562,674 A | 10/1996 | Stalcup et al. |
| 5,601,563 A | 2/1997 | Burke et al. |
| 5,632,745 A | 5/1997 | Schwartz |
| 5,683,397 A | 11/1997 | Vendrely et al. |
| 5,683,466 A | 11/1997 | Vitale |
| 5,702,460 A | 12/1997 | Carls et al. |
| 5,725,376 A | 3/1998 | Poirier |
| 5,733,292 A | 3/1998 | Gustilo et al. |
| 5,768,134 A | 6/1998 | Swaelens et al. |
| 5,776,201 A | 7/1998 | Colleran et al. |
| 5,791,212 A | 8/1998 | Han |
| 5,817,097 A | 10/1998 | Howard et al. |
| 5,824,085 A | 10/1998 | Sahay et al. |
| 5,869,170 A | 2/1999 | Cima et al. |
| 5,879,393 A | 3/1999 | Whiteside et al. |
| 5,885,296 A | 3/1999 | Masini |
| 5,897,559 A | 4/1999 | Masini |
| 5,925,049 A | 7/1999 | Gustilo et al. |
| 5,942,370 A | 8/1999 | Neckers et al. |
| 5,980,526 A | 11/1999 | Johnson et al. |
| 5,989,261 A | 11/1999 | Walker et al. |
| 6,007,537 A | 12/1999 | Burkinshaw et al. |
| 6,080,196 A | 6/2000 | Bertin |
| 6,081,577 A | 6/2000 | Webber |
| 6,096,043 A | 8/2000 | Techiera et al. |
| 6,099,313 A | 8/2000 | Dörken et al. |
| 6,139,574 A | 10/2000 | Vacanti et al. |
| 6,161,080 A | 12/2000 | Aouni et al. |
| 6,176,874 B1 | 1/2001 | Vacanti et al. |
| 6,177,034 B1 | 1/2001 | Ferrone |
| 6,206,927 B1 | 3/2001 | Fell et al. |
| 6,220,122 B1 | 4/2001 | Forsell et al. |
| 6,241,735 B1 | 6/2001 | Marmulla |
| 6,244,141 B1 | 6/2001 | Han |
| 6,251,143 B1 | 6/2001 | Schwartz et al. |
| 6,319,006 B1 | 11/2001 | Scherer et al. |
| 6,322,728 B1 | 11/2001 | Brodkin et al. |
| 6,327,491 B1 | 12/2001 | Franklin et al. |
| 6,382,975 B1 | 5/2002 | Poirier |
| 6,454,811 B1 | 9/2002 | Sherwood et al. |
| 6,463,351 B1 | 10/2002 | Clynch |
| 6,478,799 B1 | 11/2002 | Williamson |
| 6,510,334 B1 | 1/2003 | Schuster et al. |
| 6,530,958 B1 | 3/2003 | Cima et al. |
| 6,554,837 B1 | 4/2003 | Hauri et al. |
| 6,554,838 B2 | 4/2003 | McGovern et al. |
| 6,558,391 B2 | 5/2003 | Axelson et al. |
| 6,626,945 B2 | 9/2003 | Simon et al. |
| 6,668,941 B2 | 12/2003 | Phillips et al. |
| 6,679,917 B2 | 1/2004 | Ek |
| 6,711,432 B1 | 3/2004 | Krause et al. |
| 6,712,824 B2 | 3/2004 | Millard et al. |
| 6,712,856 B1 | 3/2004 | Carignan et al. |
| 6,738,657 B1 | 5/2004 | Franklin et al. |
| 6,766,878 B2 | 7/2004 | Widmer et al. |
| 6,772,026 B2 | 8/2004 | Bradbury et al. |
| 6,814,735 B1 | 11/2004 | Zirngibl et al. |
| 6,916,324 B2 | 7/2005 | Sanford et al. |
| 6,994,549 B2 | 2/2006 | Brodkin et al. |
| 7,060,074 B2 | 6/2006 | Rosa et al. |
| 7,141,053 B2 | 11/2006 | Rosa et al. |
| 7,172,597 B2 | 2/2007 | Sanford |
| 7,175,435 B2 | 2/2007 | Andersson et al. |
| 7,194,295 B2 | 3/2007 | Vilsmeier |
| 7,534,263 B2 | 5/2009 | Burdulis, Jr. et al. |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,824,181 B2 | 11/2010 | Sers |
| 7,981,158 B2 | 7/2011 | Fitz et al. |
| 7,988,691 B2 | 8/2011 | Schulze et al. |
| 8,496,663 B2 | 7/2013 | White et al. |
| 2002/0007294 A1 | 1/2002 | Bradbury et al. |
| 2002/0059049 A1 | 5/2002 | Bradbury et al. |
| 2002/0183760 A1 | 12/2002 | McGovern et al. |
| 2003/0055501 A1 | 3/2003 | Fell et al. |
| 2003/0225413 A1 | 12/2003 | Sanford et al. |
| 2004/0039259 A1 | 2/2004 | Krause et al. |
| 2004/0092932 A1 | 5/2004 | Aubin et al. |
| 2004/0153087 A1 | 8/2004 | Sanford et al. |
| 2004/0181144 A1 | 9/2004 | Cinquin et al. |
| 2004/0185422 A1 | 9/2004 | Orth et al. |
| 2004/0204760 A1 | 10/2004 | Fitz et al. |
| 2004/0236424 A1 | 11/2004 | Berez et al. |
| 2004/0249385 A1 | 12/2004 | Faoro |
| 2004/0260301 A1 | 12/2004 | Lionberger et al. |
| 2005/0015003 A1 | 1/2005 | Lachner et al. |
| 2005/0037320 A1 | 2/2005 | Poirier |
| 2005/0043835 A1 | 2/2005 | Christensen |
| 2005/0133955 A1 | 6/2005 | Christensen |
| 2005/0170311 A1 | 8/2005 | Tardieu et al. |
| 2005/0171545 A1 | 8/2005 | Walsh et al. |
| 2005/0234461 A1 | 10/2005 | Burdulis, Jr. et al. |
| 2005/0261697 A1 | 11/2005 | Canonaco et al. |
| 2005/0267584 A1 | 12/2005 | Burdulis et al. |
| 2006/0089621 A1 | 4/2006 | Fard |
| 2006/0245627 A1 | 11/2006 | Nagamune |
| 2007/0006887 A1 | 1/2007 | Frank |
| 2007/0059665 A1 | 3/2007 | Orentlicher et al. |
| 2007/0198022 A1 | 8/2007 | Lang et al. |
| 2007/0213738 A1 | 9/2007 | Martin et al. |
| 2007/0226986 A1 | 10/2007 | Park et al. |
| 2007/0233140 A1 | 10/2007 | Metzger et al. |
| 2007/0233141 A1 | 10/2007 | Park et al. |
| 2007/0250169 A1 | 10/2007 | Lang |
| 2007/0288030 A1 | 12/2007 | Metzger et al. |
| 2008/0015602 A1 | 1/2008 | Axelson |
| 2008/0015607 A1 | 1/2008 | D'Alessio et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0183177 A1 | 7/2008 | Fox et al. |
| 2008/0195107 A1 | 8/2008 | Cuckler et al. |
| 2008/0228189 A1 | 9/2008 | Fox et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0306558 A1 | 12/2008 | Hakki |
| 2008/0312659 A1 | 12/2008 | Metzger et al. |

(56) References Cited

U.S. PATENT DOCUMENTS

| | | |
|---|---|---|
| 2009/0018546 A1 | 1/2009 | Daley |
| 2009/0024131 A1 | 1/2009 | Metzger et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0164024 A1 | 6/2009 | Rudan et al. |
| 2009/0222014 A1 | 9/2009 | Bojarski et al. |
| 2009/0222016 A1 | 9/2009 | Park et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0307893 A1 | 12/2009 | Burdulis, Jr. et al. |
| 2010/0016947 A1 | 1/2010 | Dobak et al. |
| 2010/0023015 A1 | 1/2010 | Park |
| 2010/0087829 A1 | 4/2010 | Metzger et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2011/0015636 A1 | 1/2011 | Katrana et al. |
| 2011/0015639 A1 | 1/2011 | Metzger et al. |
| 2011/0029091 A1 | 2/2011 | Bojarski et al. |
| 2011/0029116 A1 | 2/2011 | Jordan et al. |
| 2011/0054478 A1 | 3/2011 | Vanasse et al. |
| 2011/0066193 A1 | 3/2011 | Lang et al. |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2012/0029520 A1 | 2/2012 | Lang et al. |
| 2013/0296873 A1 | 11/2013 | White et al. |
| 2014/0142579 A1 | 5/2014 | White et al. |
| 2016/0220262 A1 | 8/2016 | White et al. |

FOREIGN PATENT DOCUMENTS

| | | |
|---|---|---|
| DE | 3902249 A1 | 8/1990 |
| DE | 4016704 C1 | 9/1991 |
| DE | 3717871 C3 | 5/1995 |
| EP | 97001 A1 | 12/1983 |
| EP | 337901 A1 | 10/1989 |
| EP | 0645984 | 4/1995 |
| EP | 756735 | 2/1997 |
| EP | 0908836 A2 | 4/1999 |
| EP | 1013231 A2 | 6/2000 |
| EP | 1136041 A2 | 9/2001 |
| EP | 904158 B1 | 7/2002 |
| EP | 709061 B1 | 7/2003 |
| EP | 1348393 A1 | 10/2003 |
| EP | 1486900 A1 | 12/2004 |
| EP | 1498851 A1 | 1/2005 |
| EP | 1444957 B1 | 3/2007 |
| EP | 1938749 A2 | 7/2008 |
| EP | 1669033 B1 | 2/2009 |
| FR | 2819168 A1 | 7/2002 |
| GB | 2426200 A | 11/2006 |
| GB | 2437003 A | 10/2007 |
| GB | 2447702 | 9/2008 |
| WO | 8911257 A1 | 11/1989 |
| WO | 9325157 A1 | 12/1993 |
| WO | 9528688 A1 | 10/1995 |
| WO | 9800072 A1 | 1/1998 |
| WO | 9832384 A1 | 7/1998 |
| WO | 9932045 A1 | 7/1999 |
| WO | 2004000139 A1 | 12/2003 |
| WO | 2004032806 A1 | 4/2004 |
| WO | 2004017842 A2 | 6/2004 |
| WO | 2004049981 A2 | 6/2004 |
| WO | 2004075771 A1 | 9/2004 |
| WO | 2005018453 A1 | 3/2005 |
| WO | 2005051239 A1 | 6/2005 |
| WO | 2005051240 A1 | 6/2005 |
| WO | 2005053564 A2 | 6/2005 |
| WO | 2005084558 A1 | 9/2005 |
| WO | 2006058057 A2 | 6/2006 |
| WO | 2006060795 A1 | 6/2006 |
| WO | 2007092841 A2 | 8/2007 |
| WO | 2007097853 A2 | 8/2007 |
| WO | 2007097854 A2 | 8/2007 |
| WO | 2007145937 A2 | 12/2007 |
| WO | 2008021494 A2 | 2/2008 |
| WO | 2008112996 A1 | 9/2008 |
| WO | 2008117028 | 10/2008 |
| WO | 2008117028 A1 | 10/2008 |
| WO | 2009001083 A1 | 12/2008 |
| WO | 2009045960 A1 | 4/2009 |
| WO | 2009111512 A2 | 9/2009 |
| WO | 2009129063 A1 | 10/2009 |
| WO | 2009129067 A1 | 10/2009 |
| WO | 2010014808 A2 | 2/2010 |
| WO | 2010033431 A1 | 3/2010 |

OTHER PUBLICATIONS

Radermacher et al., "Computer-Integrated Orthopaedic Surgery: Connection of Planning and Execution in Surgical Intervention," Computer Integrated Surgery, 451-463, 1995.

Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P. Nolte and R. Ganz, eds, 42-52, Hogrefe & Huber Publishing 1999.

Hafez et al., "Computer-assisted Total Kneed Arthroplasty Using Patient-specific Templating", Clinical Orthopaedics and Related Research, 444, 184-192, 2006 (12 pages).

European Search Report, European Application No. 12174187.0-2310, Oct. 2, 2012, 6 pages.

BIOMET, Signature Personalized Patient Care, Surgical Technique Addendum to the Vanguard Complete Knee System, Jul. 2008, 12 pages.

Australian Patent Examination Report No. 1 issued in connection with Australian Patent Application No. 2015203489, Dated Jul. 18, 2016, 4 pages.

Sharma et al.; The Role of Knee Alignment in Disease Progression and Functional Decline in Knee Osteoarthritis; Jul. 11, 2001; American Medical Association; 10 pages.

Hube et al.; Orthopaedic Surgery The Essentials, Chaper 36 Knee Reconstruction; 1999; 12 pages.

Corin Medical Limited; The Corin X-ActTM Instrumentation and Operative Technique; Nov. 1998; 9 pages.

Kraus et al.; A Comparative Assessment of Alignment Angle of the Knee by Radiographic and Physical Examination Methods; Jun. 6, 2005; 6 pages.

(56) References Cited

OTHER PUBLICATIONS

Depuy; LCS Total Knee System—Surgical Procedure; 1989; 36 pages.
Engh et al.; Legent II Surgical Technique; The Concept of Personalization—Total Knee Replacement Using the AMK-Legend II; 1992; 31 pages.
Lotke; Knee Arthroplasty; Primary Total Knees—Standard Principles and Techniques; Raven Press, Ltd.; 5 pages; 1995.
Mills et al.; Use of Computer Tomographic Reconstruction in Planning Osteotomies of the Hip; Jan. 1992; 6 pages.
Portheine et al.; Development of a clinical demonstrator fro computer assisted orthopedic surgery with CT-image based individual templates; 1997; 6 pages.
Radermacher et al.; Computer Assisted Matching of Planning and Execution in Orthopedic Surgery; 1993; 2 pages.
Radermacher et al.; Computer Assisted Orthopaedic Surgery with Image Based Individual Templates; No. 354, pp. 28-38; 1998; 11 pages.
Radermacher, Klaus, et al. "Computer Assisted Orthopaedic Individual Templates." Clinical Orthopaedics and Related Research. (Sep. 1998) No. 354; pp. 28-38.
Radermacher, "Template Based Navigation—An Efficient Technique for Hip and Knee Surgery", CAOS First Asian Meet, India, Mar. 27-28, 2004, pp. 44-50.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", 2.sup.nd European Conference on Eng. and Med., presented Apr. 26, 1993, 12 pages.
Radermacher et al., "Surgical Therapy Technology", Helmholtz-Institut Aachen Research Report, 1993-1994, pp. 189-219.
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.
Radermacher et al., English Translation with Certification: "Computer-assisted operative interventions in orthopedics—we there prospects for endoprosthetics as well?", Prac. Ortho., vol. 27, pp. 1-17, 1997.
Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al., In German: "Computer-Assisted Planning and Operation in Orthopedics", Orth. Prac. 36th year, pp. 731-737, Dec. 2000.
Radermacher et al., English Translation with Certification: "Computer-Assisted Planning and Operation in Orthopedics", Orth. Prac. 36th year, pp. 731-737, Dec. 2000.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996. cited by applicant.
Radermacher et al., "CT Image Based Planning and Execution of Interventions in Orthopedic Surgery Using Individual Templates—Experimental Results and a spects of Clinical Applications." In Nolte LP, Ganz, R. (eds). CAOS—Computer Assisted Orthopaedic Surgery. Bern, Hans Huber (in Press) 1998. cited by applicant.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher, German Version: Helmholtz Institute of Biomedical Technology, "Computer-Assisted Planning and Execution of Orthopedic Surgery Using Individual Surgical Templates", May 18, 1999.
Radermacher, English Translation: Helmholtz Institute of Biomedical Technology, "Computer-Assisted Planning and Execution of Orthopedic Surgery Using Individual Surgical Templates", May 18, 1999.
Radermacher et al., "Computer Assisted Orthopedic Surgery by Means of Individual Templates—Aspects and Analysis of Potential Applications—" Proceedings of the First International Symposium on Medical Robotics and Computer Assisted Surgery, vol. 1: Sessions I-III, MRCAS '94, Pittsburgh, PA, pp. 42-48 (Sep. 22-24, 1994).

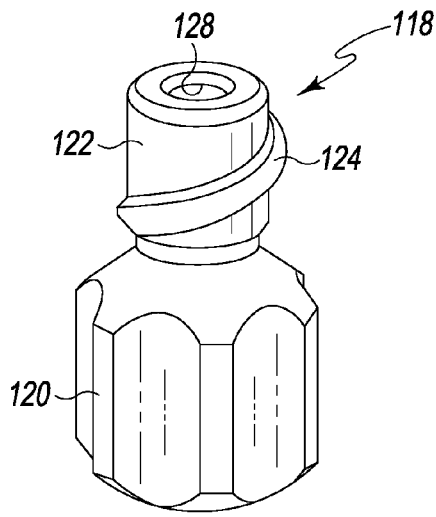
Fig. 13
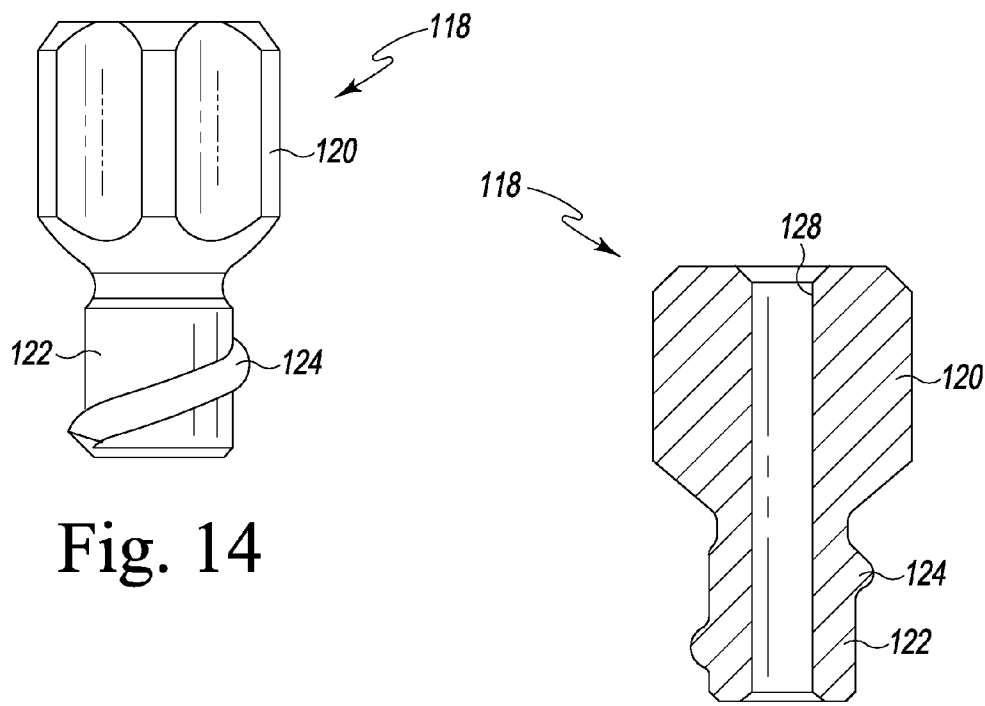
Fig. 14
Fig. 15

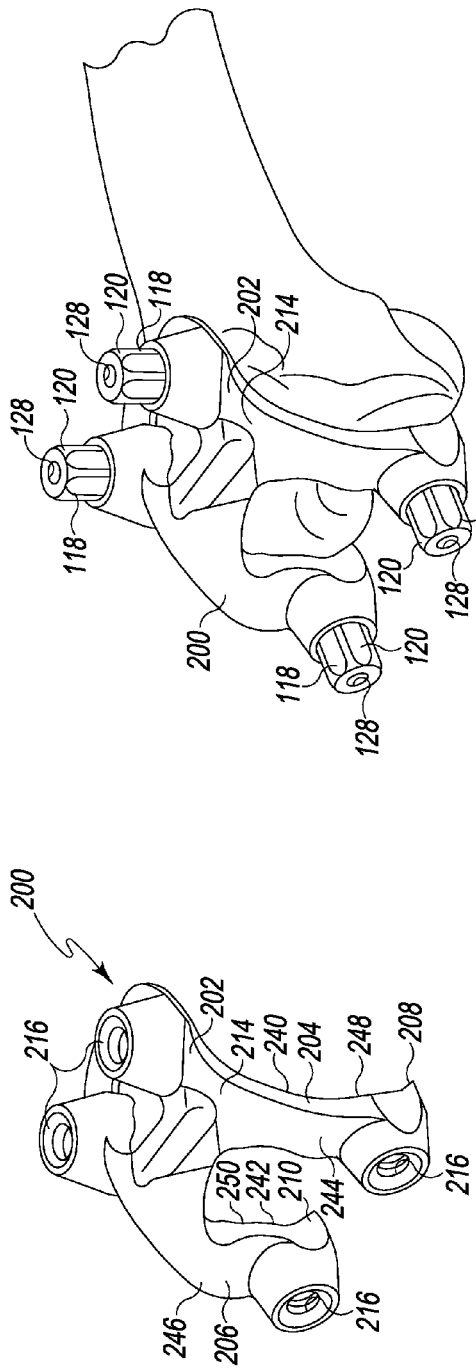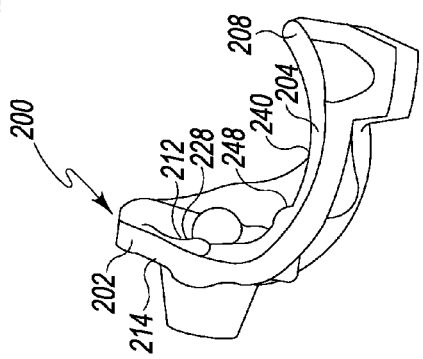

CUSTOMIZED PATIENT-SPECIFIC ORTHOPAEDIC PIN GUIDES

This application is a divisional of and claims priority to U.S. patent application Ser. No. 14/155,656, which was filed on Jan. 15, 2014, which is a continuation of and claims priority to U.S. patent application Ser. No. 13/173,880, which was filed on Jun. 30, 2011 and issued as U.S. Pat. No. 8,641,721 on Feb. 4, 2014, and is expressly incorporated herein by reference.

TECHNICAL FIELD

The present disclosure relates generally to customized patient-specific orthopaedic surgical instruments, and in particular to customized patient-specific orthopaedic pin guides.

BACKGROUND

Joint arthroplasty is a well-known surgical procedure by which a diseased and/or damaged natural joint is replaced by a prosthetic joint. A typical knee prosthesis includes a tibial tray, a femoral component, a polymer insert or bearing positioned between the tibial tray and the femoral component, and, in some cases, a polymer patella button. To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

SUMMARY

According to one aspect, a customized patient-specific orthopaedic surgical instrument includes a customized patient-specific tibial pin guide. The pin guide includes a body having a bone-facing surface that has a customized patient-specific negative contour configured to receive a portion of an anterior side of a patient's tibia that has a corresponding positive contour. The body has a first hole formed therein with a first locking slot extending in a direction parallel to the axis of the first hole. The first locking slot opens into the first hole. The body also has a second hole formed therein with a second locking slot extending in a direction parallel to the axis of the second hole. The second locking slot opens into the second hole. The customized patient-specific tibial pin guide also has a first tab extending posteriorly from the body. The first tab has a bone-facing surface that has a customized patient-specific negative contour configured to receive a first portion of the proximal side of the patient's tibia that has a corresponding positive contour. The customized patient-specific tibial pin guide also has a second tab extending posteriorly from the body, the second tab including a bone-facing surface that has a customized patient-specific negative contour configured to receive a second portion of the proximal side of the patient's tibia that has a corresponding positive contour. The customized patient-specific orthopaedic surgical instrument also includes a first removable drill bushing having a post with a locking flange extending therefrom. The post of the first removable drill bushing is positioned in the first hole of the body of the customized patient-specific tibial pin guide such that the locking flange of the first removable drill bushing is positioned in the first locking slot of the body of the customized patient-specific tibial pin guide. The customized patient-specific orthopaedic surgical instrument further includes a second removable drill bushing having a post with a locking flange extending therefrom. The post of the second removable drill bushing is positioned in the second hole of the body of the customized patient-specific tibial pin guide such that the locking flange of the second removable drill bushing is positioned in the second locking slot of the body of the customized patient-specific tibial pin guide.

The locking slots of the customized patient-specific tibial pin guide may be embodied as female threads extending helically around the periphery of the holes of the customized patient-specific tibial pin guide, with the locking flanges of the removable drill bushings being embodied as male threads extending helically around the post of the removable drill bushings. The male threads of the drill bushings are threaded into the female threads of the body so as to lock the removable drill bushings to the customized patient-specific tibial pin guide.

In an embodiment, an outer end of each of the locking slots opens into an outer surface of the body of the customized patient-specific tibial pin guide that is opposite the bone-facing surface, with an inner end of each of the locking slots defining an annular recess formed in the body of the customized patient-specific tibial pin guide. The locking flanges of the removable drill bushings may include a tab that extends outwardly from the post of the removable drill bushings, with such a tab being captured in the annular recess so as to lock the removable drill bushing to the customized patient-specific tibial pin guide.

The customized patient-specific orthopaedic tibial pin guide may be formed from a polymeric material, with both the first removable drill bushing and the second removable drill bushing being formed from a metallic material.

The body, the first tab, and the second tab of the customized patient-specific tibial pin guide may define a monolithic structure.

The body, the first tab, and the second tab of the customized patient-specific tibial pin guide may define a disposable monolithic structure.

The body, the first tab, and the second tab of the customized patient-specific tibial pin guide define a monolithic, disposable polymeric structure, with both the first removable drill bushing and the second removable drill bushing being reusable and formed from a metallic material.

The first tab and the second tab of the customized patient-specific tibial pin guide may define an opening therebetween.

The first removable drill bushing and the second removable drill bushing are positioned to allow a surgeon to install a pair of guide pins on the anterior side of the patient's tibia.

According to another aspect, a customized patient-specific orthopaedic surgical instrument includes a customized patient-specific femoral pin guide. The pin guide has a body that includes a bone-facing surface that has a customized patient-specific negative contour configured to receive a portion of an anterior side of a patient's femur that has a corresponding positive contour. The body has a first hole formed therein with a first locking slot extending in a direction parallel to the axis of the first hole. The first locking slot opens into the first hole. The body also has a second hole formed therein with a second locking slot extending in a direction parallel to the axis of the second hole. The second locking slot opens into the second hole. The customized patient-specific femoral pin guide also has a first tab extending posteriorly from the body. The first tab has a bone-facing surface that includes a customized patient-specific negative contour configured to receive a first portion of the distal side of the patient's femur that has a corresponding positive contour. The first tab has a third hole formed therein with a third locking slot extending in a direction parallel to the axis of the third hole. The third locking slot opens into the third hole. The customized patient-specific femoral pin guide also includes a second tab extending posteriorly from the body. The second tab has a bone-facing surface that includes a customized patient-specific negative contour configured to receive a second portion of the distal side of the patient's femur that has a corresponding positive contour. The second tab has a fourth hole formed therein with a fourth locking slot extending in a direction parallel to the axis of the fourth hole. The fourth locking slot opens into the fourth hole. The customized patient-specific orthopaedic surgical instrument also includes a first removable drill bushing having a post locked into the first hole. The customized patient-specific orthopaedic surgical instrument further includes a second removable drill bushing having a post locked into the second hole. The customized patient-specific orthopaedic surgical instrument includes a third removable drill bushing having a post locked into the third hole. And finally, the customized patient-specific orthopaedic surgical instrument includes a fourth removable drill bushing having a post locked into the fourth hole.

The locking slots of the customized patient-specific femoral pin guide may be embodied as female threads extending helically around the periphery of the holes of the customized patient-specific femoral pin guide, with the locking flanges of the removable drill bushings being embodied as male threads extending helically around the posts of the removable drill bushings. The male threads of the drill bushings are threaded into the female threads of the pin guide so as to lock the removable drill bushings to the customized patient-specific femoral pin guide.

In an embodiment, an outer end of each of the locking slots opens into an outer surface of the customized patient-specific femoral pin guide that is opposite the bone-facing surface, with an inner end of the locking slots defining an annular recess formed in the customized patient-specific femoral pin guide. The locking flanges of the removable drill bushings may include a tab that extends outwardly from the post of the removable drill bushings, with such a tab being captured in the annular recess so as to lock the removable drill bushing to the customized patient-specific femoral pin guide.

The body, the first tab, and the second tab of the customized patient-specific femoral pin guide may be formed from a polymeric material, with each of the first, second, third, and fourth removable drill bushings being formed from a metallic material.

The body, the first tab, and the second tab of the customized patient-specific femoral pin guide may define a monolithic structure.

The body, the first tab, and the second tab of the customized patient-specific femoral pin guide may define a disposable monolithic structure.

The body, the first tab, and the second tab of the customized patient-specific femoral pin guide may define a monolithic, disposable polymeric structure, with each of the first, second, third, and fourth removable drill bushings being reusable and formed from a metallic material.

The first tab and the second tab of the customized patient-specific femoral pin guide may define an opening therebetween.

The first removable drill bushing and the second removable drill bushing may be positioned to allow a surgeon to install a first pair of guide pins on the anterior side of the patient's tibia, with the third removable drill bushing and the fourth removable drill bushing being positioned to allow a surgeon to install a second pair of guide pins on the distal side of the patient's tibia.

According to another aspect, a method of performing an orthopaedic surgical procedure on a bone of a patient includes assembling a customized patient-specific pin guide assembly by locking a first removable drill bushing into a first hole of a customized patient-specific pin guide and then locking a second removable drill bushing into a second hole of the customized patient-specific pin guide. The assembled customized patient-specific pin guide assembly is then positioned in contact with the bone of the patient. A pair of guide pins is inserted into the bone of the patient by advancing a first guide pin of the pair of guide pins through the first removable drill bushing, and then advancing a second guide pin of the pair of guide pins through the second removable drill bushing. The customized patient-specific pin guide assembly is then removed from the bone of the patient without removing the pair of guide pins from the bone of the patient. A patient-universal cutting block is then positioned into contact with the bone of the patient such that the pair of guide pins is received into a pair of guide pin holes defined in the patient-universal cutting block. A cut is then made in the bone of the patient with the patient-universal cutting block.

The customized patient-specific pin guide assembly may be disassembled by unlocking the first removable drill bushing from the first hole of the customized patient-specific pin guide, and then unlocking the second removable drill bushing from the second hole of the customized patient-specific pin guide. The disassembled customized patient-specific pin guide assembly may be removed from the bone of the patient without removing the pair of guide pins from the bone of the patient.

The patient-universal cutting block may be removed from the bone of the patient prior to making the cut in the bone of the patient, and thereafter repositioned into contact with the bone of the patient such that the pair of guide pins is received into a second, different pair of guide pin holes defined in the patient-universal cutting block prior to making the cut in the bone of the patient. In doing so, an amount of bone to be removed from the bone of the patient may be determined subsequent to initially positioning the patient-universal cutting block into contact with the bone of the patient. The pair of second, different guide pin holes which corresponds to the amount of bone to be removed from the bone of the patient is then selected from a plurality of pairs of guide pin holes, and the patient-universal cutting block repositioned into contact with the bone of the patient such that the pair of guide pins is received into the selected second, different pair of guide pin holes defined in the patient-universal cutting block prior to making the cut in the bone of the patient.

The assembled customized patient-specific pin guide assembly may be embodied as a femoral pin guide.

The assembled customized patient-specific pin guide assembly may be embodied as a tibial pin guide.

BRIEF DESCRIPTION OF THE DRAWINGS

The detailed description particularly refers to the following figures, in which:

FIG. 13 is a perspective view of a removable drill bushing;

FIG. 14 is an elevation view of the removable drill bushing of FIG. 13;

FIG. 15 is a cross section view of the removable drill bushing of FIG. 13;

FIG. 21 is a perspective view of a customized patient-specific femoral pin guide;

FIG. 22 is a side elevation view of the customized patient-specific femoral pin guide of FIG. 21;

FIG. 23 shows the customized patient-specific femoral pin guide of FIG. 21 coupled to the femur of a patient;

DETAILED DESCRIPTION OF THE DRAWINGS

Figure 1:
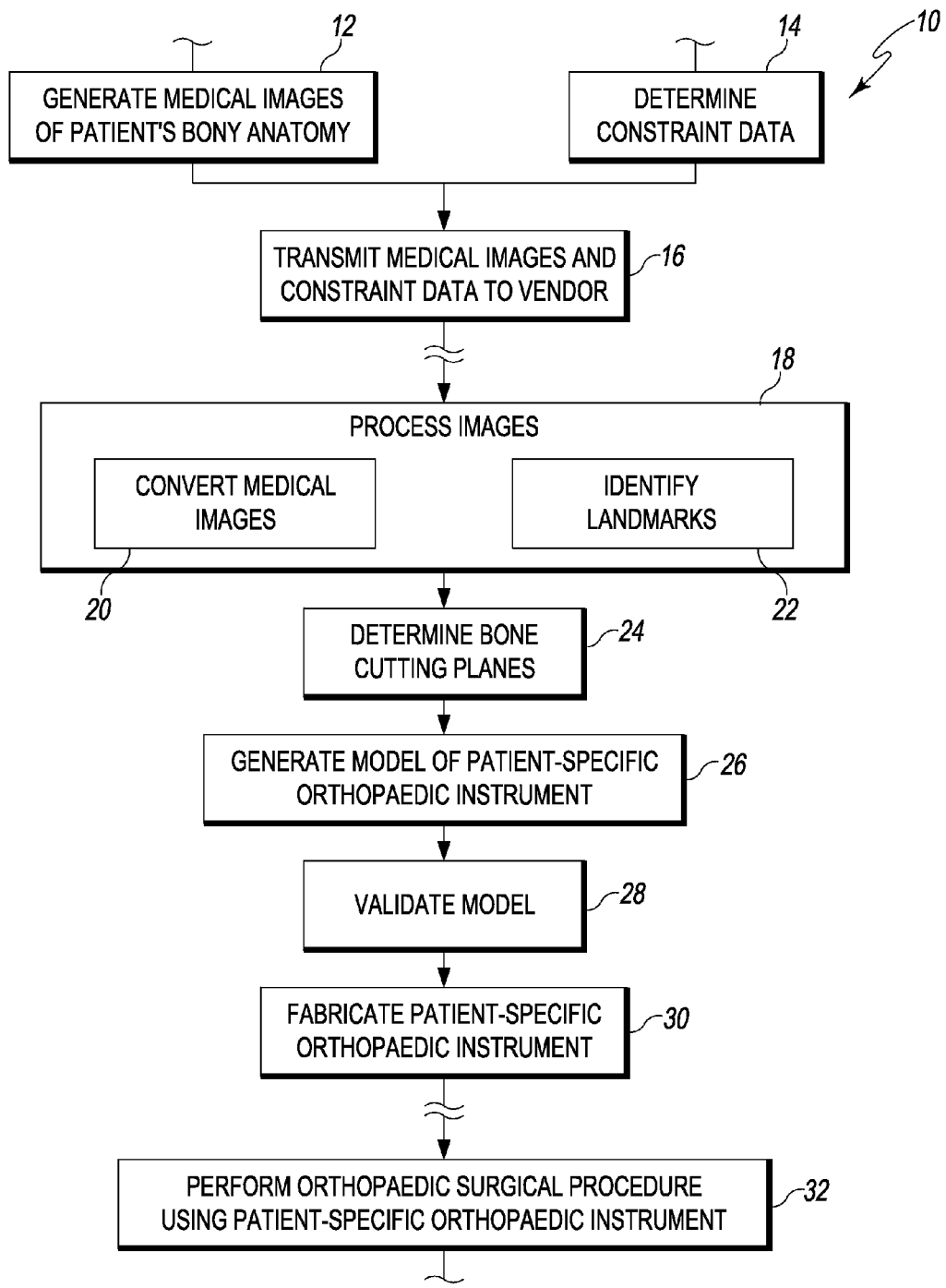
FIG. 1 is a simplified flow diagram of an algorithm for designing and fabricating a customized patient-specific orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to the orthopaedic implants and instruments described herein, along with a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses. Examples of "customized patient-specific orthopaedic surgical instruments" include customized patient-specific drill/pin guides, customized patient-specific tibial cutting blocks, and customized patient-specific femoral cutting blocks.

In some embodiments, the customized patient-specific orthopaedic surgical instrument may be customized to the particular patient based on the location at which the instrument is to be coupled to one or more bones of the patient, such as the femur and/or tibia. For example, in some embodiments, the customized patient-specific orthopaedic surgical instrument may include a bone-contacting or facing surface having a negative contour that matches or substantially matches the contour of a portion of the relevant bone of the patient. As such, the customized patient-specific orthopaedic surgical instrument is configured to be coupled to the bone of a patient in a unique location and position with respect to the patient's bone. That is, the negative contour of the bone-contacting surface is configured to receive the matching contour surface of the portion of the patient's bone. As such, the orthopaedic surgeon's guesswork and/or intra-operative decision-making with respect to the placement of the orthopaedic surgical instrument are reduced. For example, the orthopaedic surgeon may not be required to locate landmarks of the patient's bone to facilitate the placement of the orthopaedic surgical instrument, which typically requires some amount of estimation on part of the surgeon. Rather, the orthopaedic surgeon may simply couple the customized patient-specific orthopaedic surgical instrument on the bone or bones of the patient in the unique location. When so coupled, the cutting plane, drilling/pinning holes, milling holes, and/or other guides are defined in the proper location relative to the bone and intended orthopaedic prosthesis. The customized patient-specific orthopaedic surgical instrument may be embodied as any type of orthopaedic surgical instrument such as, for example, a bone-cutting block, a drilling/pin guide, a milling guide, or other type of orthopaedic surgical instrument configured to be coupled to a bone of a patient.

As shown in FIG. 1, the algorithm 10 includes process steps 12 and 14, in which an orthopaedic surgeon performs pre-operative planning of the orthopaedic surgical procedure to be performed on a patient. The process steps 12 and 14 may be performed in any order or contemporaneously with each other. In process step 12, a number of medical images of the relevant bony anatomy or joint of the patient are generated. To do so, the orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as any number of computed tomography (CT) images, magnetic resonance imaging (MRI) images, or other three-dimensional medical images. Additionally or alternatively, as discussed in more detail below in regard to process step 18, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's knee joint.

In process step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for a metal-on-metal interface, amount of inclination for implantation, the thickness of the bone to resect, size range of the orthopaedic implant, and/or the like. In some embodiments, the orthopaedic surgeon's preferences are saved as a surgeon's profile, which may used as a default constraint values for further surgical plans.

In process step 16, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer process the medical images to facilitate the determination of the bone cutting planes, implant sizing, and fabrication of the customized patient-specific orthopaedic surgical instrument as discussed in more detail below. For example, in process step 20 the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application. Further, in some embodiments, an algorithm may be used to account for tissue such as cartilage not discernable in the generated medical images. In such embodiments, any three-dimensional model of the patient-specific instrument (see, e.g., process step 26 below) may be modified according to such algorithm to increase the fit and function of the instrument.

In process step 22, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In process step 24, the cutting planes of the patient's bone are determined. The planned cutting planes are determined based on the type, size, and position of the orthopaedic prosthesis to be used during the orthopaedic surgical procedure, on the process images such as specific landmarks identified in the images, and on the constraint data supplied by the orthopaedic surgeon in process steps 14 and 16. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bony anatomy of the patient and that matches the constraint data or preferences of the orthopaedic surgeon is selected.

In addition to the type and size of the orthopaedic prosthesis, the planned location and position of the orthopaedic prosthesis relative to the patient's bony anatomy is determined. To do so, a digital template of the selected orthopaedic prosthesis may be overlaid onto one or more of the processed medical images. The vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's rotation with respect to bony landmarks such as the femoral epicondyle, posterior condyles, sulcus groove (Whiteside's line), and the mechanical axis as defined by the hip, knee, and/or ankle centers.

The planned cutting planes for the patient's bone(s) may then be determined based on the determined size, location, and orientation of the orthopaedic prosthesis. In addition, other aspects of the patient's bony anatomy, as determined in process step 22, may be used to determine or adjust the planned cutting planes. For example, the determined mechanical axis, landmarks, and/or other determined aspects of the relevant bones of the patient may be used to determine the planned cutting planes.

In process step 26, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The particular type of orthopaedic surgical instrument to be modeled and fabricated may be determined based on the orthopaedic surgical procedure to be performed, the constraint data, and/or the type of orthopaedic prosthesis to be implanted in the patient. As such, the customized patient-specific orthopaedic surgical instrument may be embodied as any type of orthopaedic surgical instrument for use in the performance of an orthopaedic surgical procedure. For example, the orthopaedic surgical instrument may be embodied as a bone-cutting block, a drilling/pinning guide, a milling guide, and/or any other type of orthopaedic surgical tool or instrument.

The particular shape of the customized patient-specific orthopaedic surgical instrument is determined based on the planned location of the orthopaedic surgical instrument relative to the patient's bony anatomy. The location of the customized patient-specific orthopaedic surgical instrument with respect to the patient's bony anatomy is determined based on the type and determined location of the orthopaedic prosthesis to be used during the orthopaedic surgical procedure. That is, the planned location of the customized patient-specific orthopaedic surgical instrument relative to the patient's bony anatomy may be selected based on, in part, the planned cutting planes of the patient's bone(s) as determined in step 24. For example, in embodiments wherein the customized patient-specific orthopaedic surgical instrument is embodied as a drilling/pinning guide (or hereinafter, simply a "pin guide") for use in conjunction with a patient-universal cutting block, the location of the orthopaedic surgical instrument is selected such that the cutting guide of the patient-universal cutting block, when installed on guide pins placed in the bone by use of the customized patient-specific pin guide, matches one or more of the planned cutting planes determined in process step 24. Additionally, the planned location of the orthopaedic surgical instrument may be based on the identified landmarks of the patient's bone identified in process step 22.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned to one or more of the bone cutting plane(s) as discussed above.

One illustrative embodiment of a method 40 for generating a model, such as a computer model, of a patient-specific orthopaedic instrument is illustrated in FIGS. 2 through 9. The method 40 begins with a step 42 in which a cartilage thickness value is determined. The cartilage thickness value is indicative of the average thickness of the cartilage of the patient's bone. As such, in one embodiment, the cartilage thickness value is equal to the average thickness of cartilage for an individual having similar characteristics as the patient. For example, the cartilage thickness value may be equal to the average thickness value of individuals of the same gender as the patient, the same age as the patient, having the same activity level of the patient, and/or the like. In other embodiments, the cartilage thickness value is determined based on one or more medical images of the patient's bone, such as those images transmitted in process step 16.

In step 44, a reference contour of the patient's relevant bone is determined. The reference contour is based on the surface contour of a three-dimensional model of the patient's relevant bone, such as the three-dimensional model generated in step 20. Initially the reference contour is identical to a region (i.e. the region of interest such as the distal end of the patient's femur or the proximal end of the patient's tibia) of the patient's bone. That is, in some embodiments, the reference contour is juxtaposed on the surface contour of the region of the patient's bone.

Subsequently, in step 46, the reference contour is scaled to compensate for the cartilage thickness value determined in step 42. To do so, in one embodiment, the scale of the reference contour is increased based on the cartilage thickness value. For example, the scale of the reference contour may be increased by an amount equal to or determined from the cartilage thickness value. However, in other embodiments, the reference contour may be scaled using other techniques designed to scale the reference contour to a size at which the reference contour is compensated for the thickness of the cartilage on the patient's bone.

Figure 3:
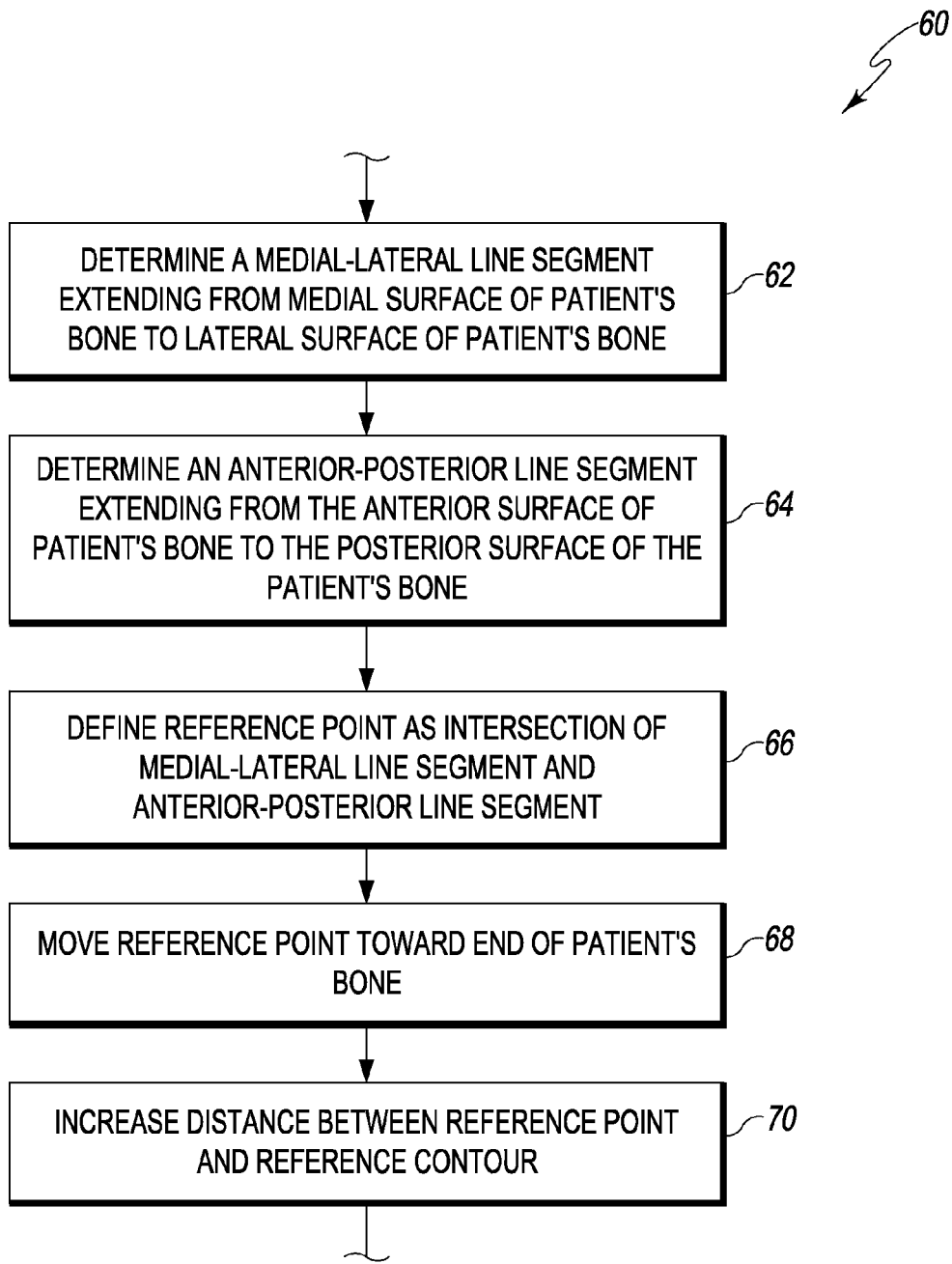
FIG. 3 is a simplified flow diagram of a method for scaling a reference contour.

For example, in one particular embodiment, the reference contour is scaled by increasing the distance between a fixed reference point and a point lying on, and defining in part, the reference contour. To do so, in one embodiment, a method 60 for scaling a reference contour as illustrated in FIG. 3 may be used. The method 60 begins with step 62 in which a medial/lateral line segment is established on the three-dimensional model of the patient's relevant bone. The medial/lateral line segment is defined or otherwise selected so as to extend from a point lying on the medial surface of the patient's bone to a point lying on lateral surface of the patient's bone. The medial surface point and the lateral surface point may be selected so as to define the substantially maximum local medial/lateral width of the patient's bone in some embodiments.

In step 64, an anterior/posterior line segment is established on the three-dimensional model of the patient's relevant bone. The anterior/posterior line segment is defined or otherwise selected so as to extend from a point lying on the anterior surface of the patient's bone to a point lying on posterior surface of the patient's bone. The anterior surface point and the posterior surface point may be selected so as to define the substantially maximum local anterior/posterior width of the patient's bone in some embodiments.

The reference point from which the reference contour will be scaled is defined in step 66 as the intersection point of the medial/lateral line segment and anterior/posterior line segment. As such, it should be appreciated that the medial surface point, the lateral surface point, the anterior surface point, and the posterior surface point lie on the same plane. After the reference point is initially established in step 66, the reference point is moved or otherwise translated toward an end of the patient's bone. For example, in embodiments wherein the patient's bone is embodied as a femur, the reference point is moved inferiorly toward the distal end of the patient's femur. Conversely, in embodiments when the patient's bone is embodied as a tibia, the reference point is moved superiorly toward the proximal end of the patient's tibia. In one embodiment, the reference point is moved a distance equal to about half the length of the anterior/posterior line segment as determined in step 64. However, in other embodiments, the reference point may be moved other distances sufficient to compensate the reference contour for thickness of the cartilage present on the patient's bone.

Once the location of the reference point has been determined in step 68, the distance between the reference point and each point lying on, and defining in part, the reference contour is increased in step 70. To do so, in one particular embodiment, each point of the reference contour is moved a distance away from the reference point based on a percentage value of the original distance defined between the reference point and the particular point on the reference contour. For example, in one embodiment, each point lying on, and defining in part, the reference contour is moved away from the reference point in by a distance equal to a percentage value of the original distance between the reference point and the particular point. In one embodiment, the percentage value is in the range of about five percent to about thirty percent. In one particular embodiment, the percentage value is about ten percent.

Figure 4:
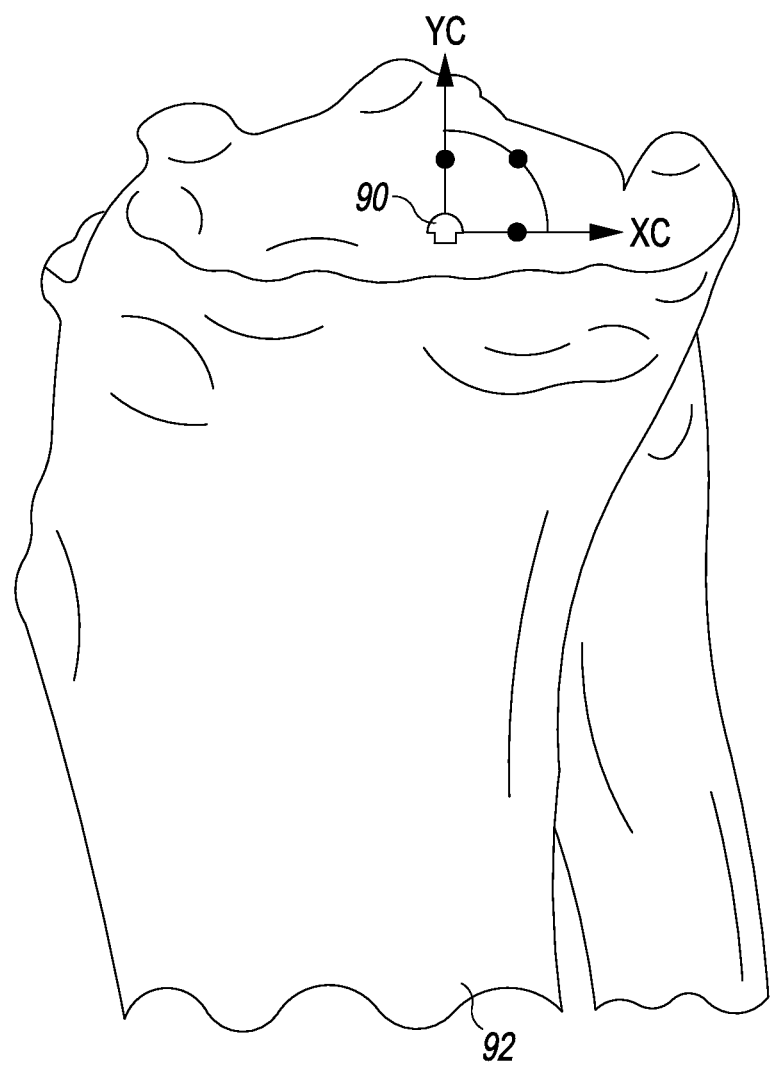
FIGS. 4-6 are three-dimensional model's of a patient's tibia.
Figure 5:
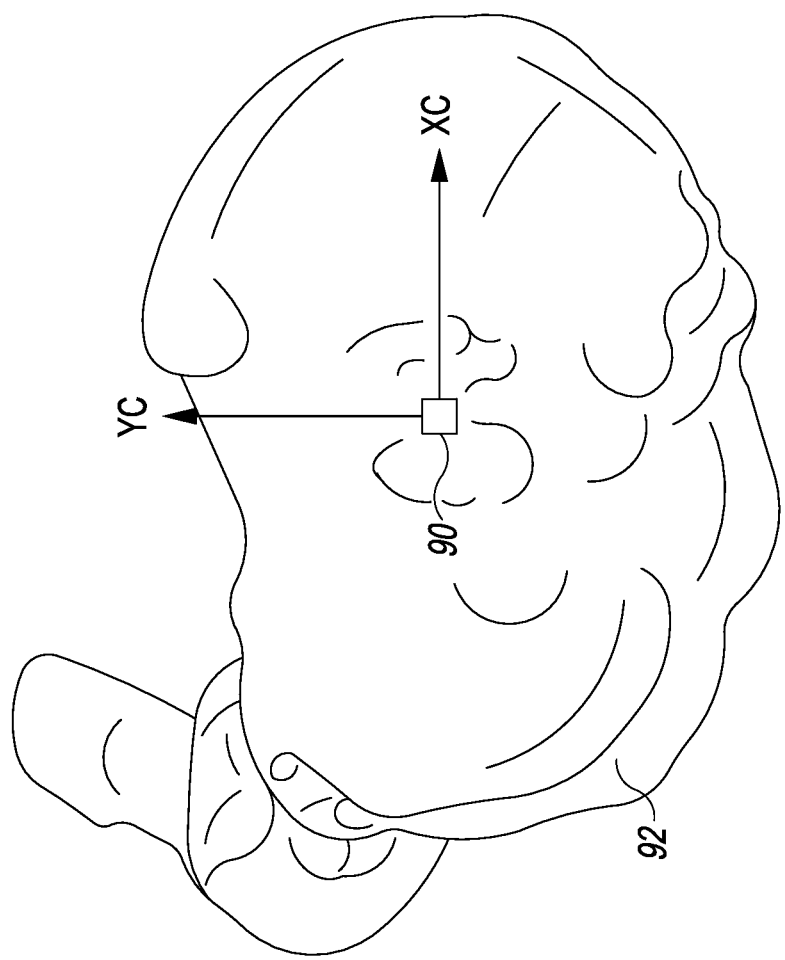
Figure 6:
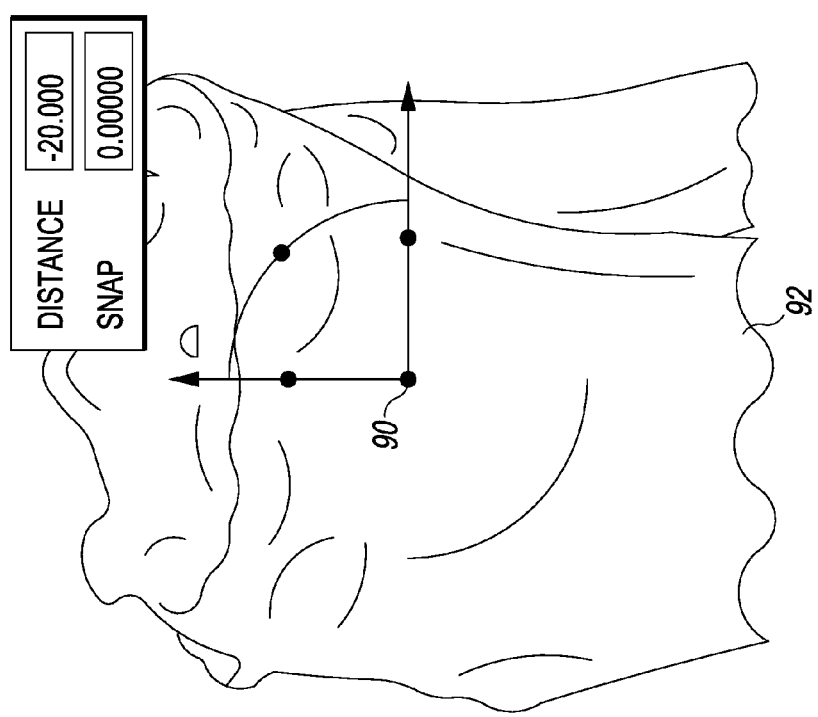

Referring now to FIGS. 4-9, in another embodiment, the reference contour is scaled by manually selecting a local "high" point on the surface contour of the three-dimensional image of the patient's bone. For example, in embodiments wherein the relevant patient's bone is embodied as a tibia as illustrated in FIGS. 4-6, the reference point 90 is initially located on the tibial plateau high point of the tibial model 92. Either side of the tibial plateau may be used. Once the reference point 90 is initially established on the tibial plateau high point, the reference point 90 is translated to the approximate center of the plateau as illustrated in FIG. 5 such that the Z-axis defining the reference point is parallel to the mechanical axis of the tibial model 92. Subsequently, as illustrated in FIG. 6, the reference point is moved in the distal direction by a predetermined amount. In one particular embodiment, the reference point is moved is the distal direction by about 20 millimeters, but other distances may be used in other embodiments. For example, the distance over which the reference point is moved may be based on the cartilage thickness value in some embodiments.

Figure 7:
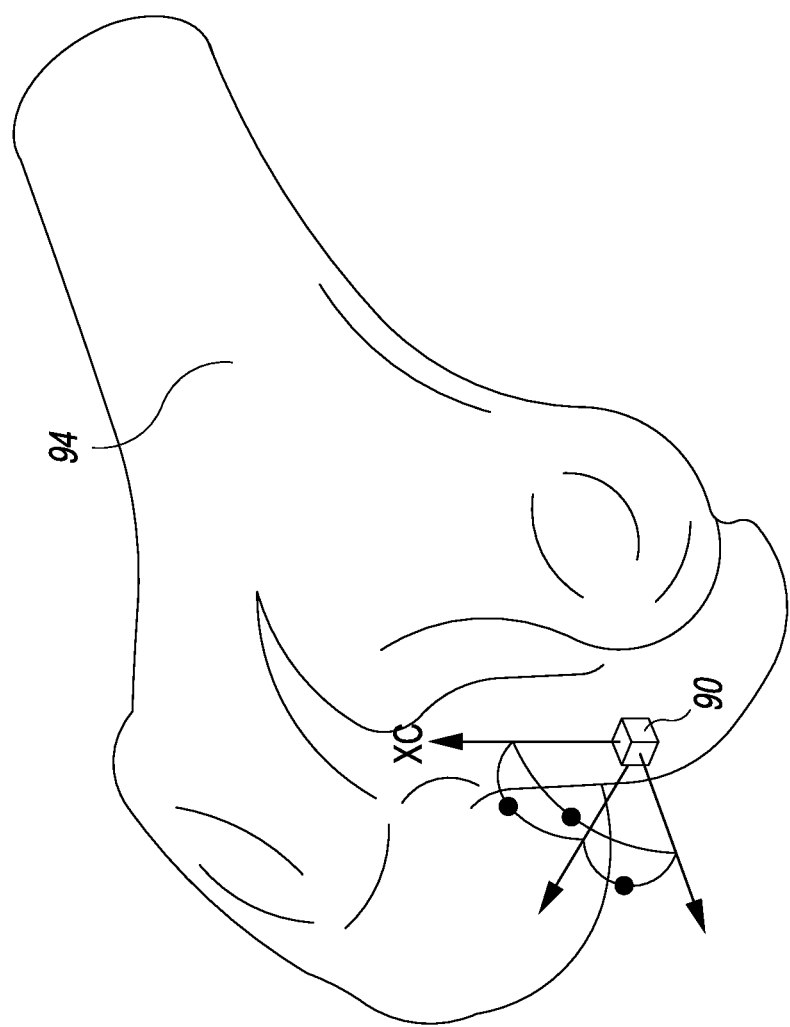
FIG. 7-9 are three-dimensional models of a patient's femur.
Figure 8:
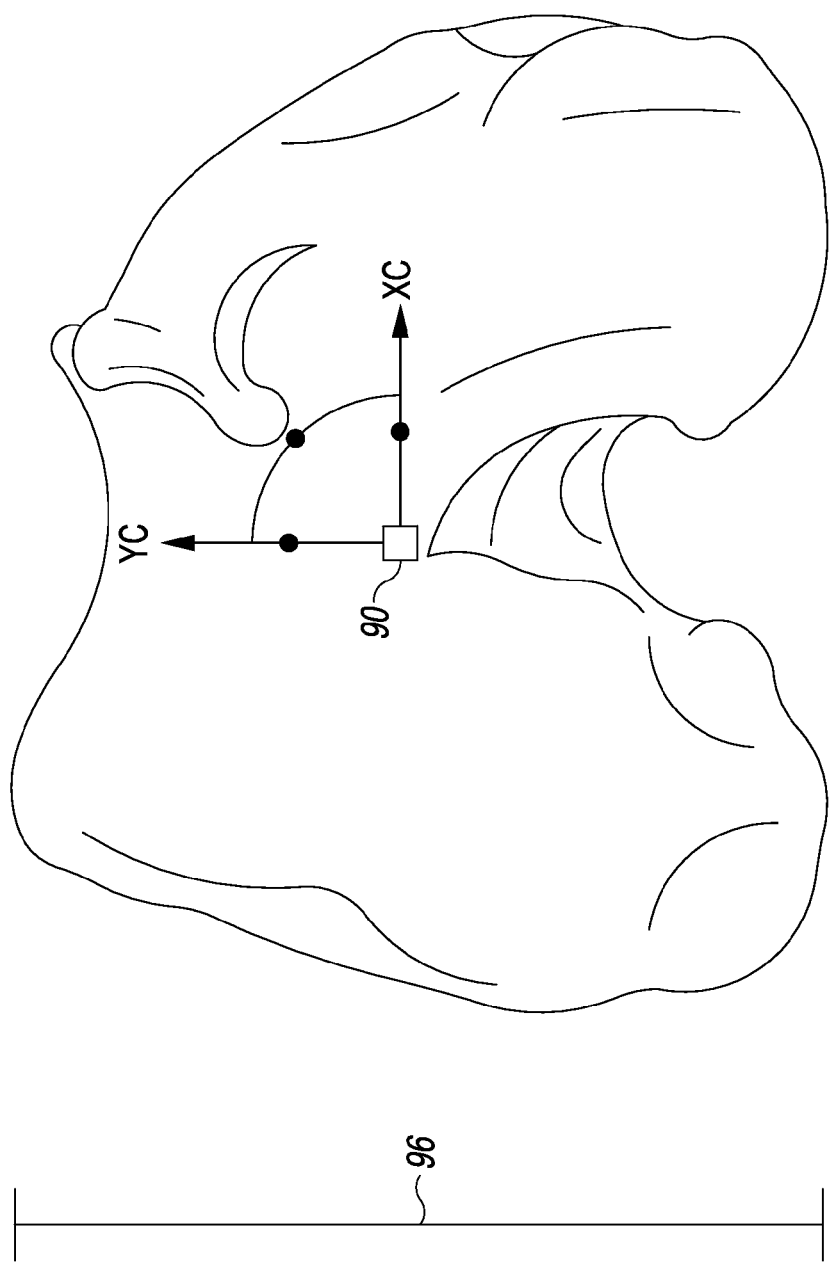
Figure 9:
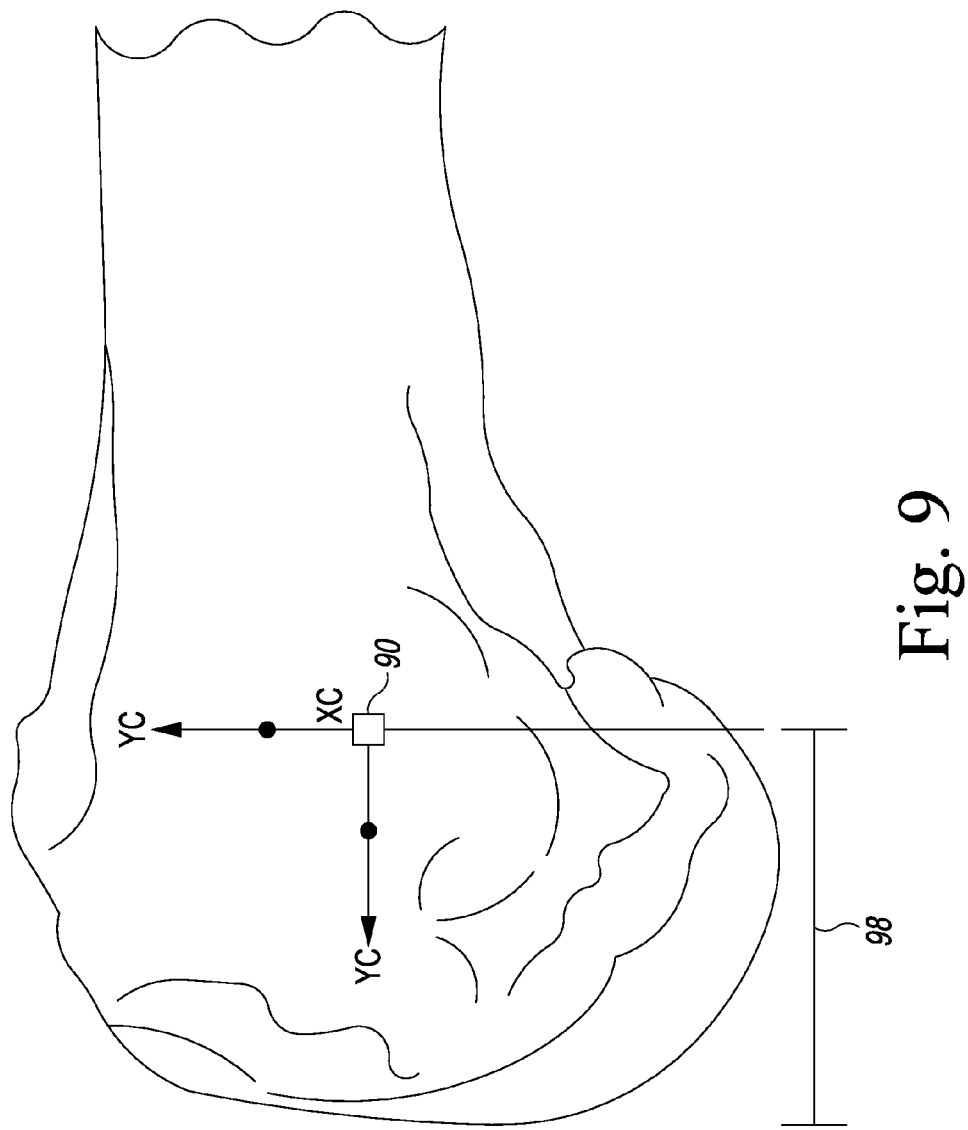

Conversely, in embodiments wherein the relevant patient's bone is embodied as a femur as illustrated in FIGS. 7-9, the reference point 90 is initially located on the most distal point of the distal end of the femoral model 94. Either condyle of the femoral model 94 may be used in various embodiments. Once the reference point 90 is initially established on the most distal point, the reference point 90 is translated to the approximate center of the distal end of the femoral model 94 as illustrated in FIG. 8 such that the Z-axis defining the reference point 90 is parallel to the mechanical axis of the femoral model 92. The anterior-posterior width 96 of the distal end of the femoral model 94 is also determined. Subsequently, as illustrated in FIG. 9, the reference point is moved or otherwise translated in the proximal or superior direction by a distance 98. In one particular embodiment, the reference point is moved in the distal or superior direction by a distance 98 equal to about half the distance 96. As such, it should be appreciated that one of a number of different techniques may be used to define the location of the reference point based on, for example, the type of bone.

Figure 2:
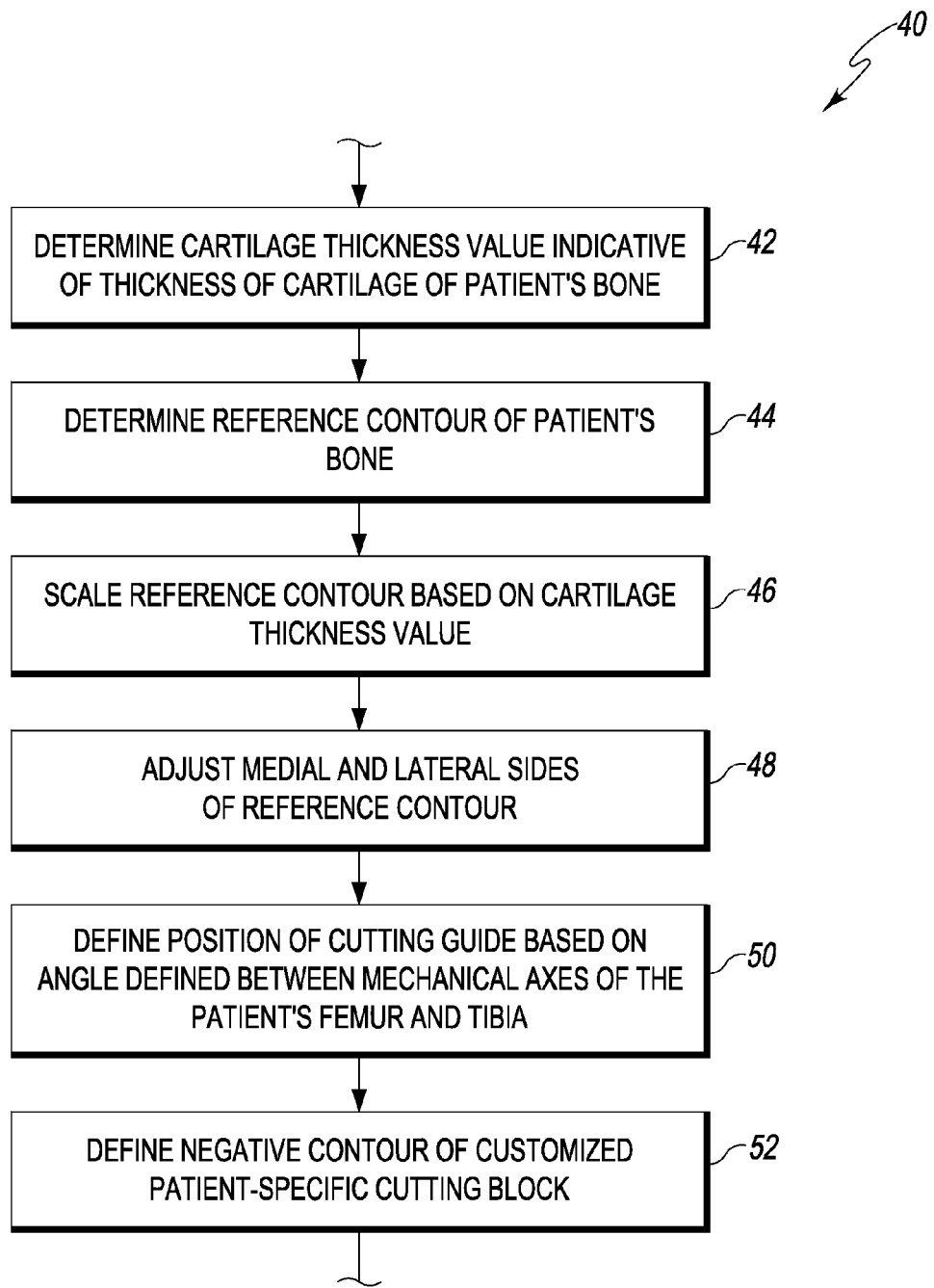
FIG. 2 is a simplified flow diagram of a method for generating a model of a patient-specific orthopaedic instrument.

Referring now back to FIG. 2, once the reference contour has been scaled in step 46, the medial/lateral sides of the reference contour are adjusted in step 48. To do so, in one embodiment, the distance between the reference point and each point lying on, and defining in part, the medial side and lateral side of the reference contour is decreased. For example, in some embodiments, the distance between the reference point and the points on the medial and lateral sides of the scaled reference contour are decreased to the original distance between such points. As such, it should be appreciated that the reference contour is offset or otherwise enlarged with respect to the anterior side of the patient's bone and substantially matches or is otherwise not scaled with respect to the medial and lateral sides of the patient's bone.

The reference contour may also be adjusted in step 48 for areas of the patient's bone having a reduced thickness of cartilage. Such areas of reduced cartilage thickness may be determined based on the existence of bone-on-bone contact as identified in a medical image, simulation, or the like. Additionally, information indicative of such areas may be provided by the orthopaedic surgeon based on his/her expertise. If one or more areas of reduced cartilage thickness are identified, the reference contour corresponding to such areas of the patient's bone is reduced (i.e., scaled back or down).

Additionally, in some embodiments, one or more osteophytes on the patient's bone may be identified; and the reference contour may be compensated for such presence of the osteophytes. By compensating for such osteophytes, the reference contour more closely matches the surface contour of the patient's bone. Further, in some embodiments, a distal end (in embodiments wherein the patient's bone is embodied as a tibia) or a proximal end (in embodiments wherein the patient's bone is embodied as a femur) of the reference contour may be adjusted to increase the conformity of the reference contour to the surface contour of the bone. For example, in embodiments wherein the patient's bone is a femur, the superior end of the scaled reference contour may be reduced or otherwise moved closer to the surface contour of the patient's femur in the region located superiorly to a cartilage demarcation line defined on the patient's femur. Conversely, in embodiments wherein the patient's bone is embodied as a tibia, an inferior end of the scaled reference contour may be reduced or otherwise moved closer to the surface contour of the patient's tibia in the region located inferiorly to a cartilage demarcation line of the patient's tibia. As such, it should be appreciated that the scaled reference contour is initially enlarged to compensate for the thickness of the patient's cartilage on the patient's bone. Portions of the scaled reference contour are then reduced or otherwise moved back to original positions and/or toward the reference point in those areas where cartilage is lacking, reduced, or otherwise not present.

Once the reference contour has been scaled and adjusted in steps 46 and 48, the position of the cutting guide is defined in step 50. In particular, the position of the cutting guide is defined based on an angle defined between a mechanical axis of the patient's femur and a mechanical axis of the patient's tibia. The angle may be determined by establishing a line segment or ray originating from the proximal end of the patient's femur to the distal end of the patient's femur and defining a second line segment or ray extending from the patient's ankle through the proximal end of the patient's tibia. The angle defined by these two line segments/rays is equal to the angle defined between the mechanical axis of the patient's femur and tibia. The position of the bone cutting guide is then determined based on the angle between the mechanical axes of the patient's femur and tibia. It should be appreciated that, as will be discussed below in more detail, the position of the cutting guide defines the position and orientation of the cutting plane of a patient-universal cutting block when it is installed on guide pins placed in the bone by use of a customized patient-specific pin guide. Subsequently, in step 52, a negative contour of the customized patient-specific pin guide is defined based on the scaled and adjusted reference contour and the angle defined between the mechanical axis of the femur and tibia.

Referring back to FIG. 1, after the model of the customized patient-specific orthopaedic surgical instrument has been generated in process step 26, the model is validated in process step 28. The model may be validated by, for example, analyzing the rendered model while coupled to the three-dimensional model of the patient's anatomy to verify the correlation of cutting guides and planes, drilling guides and planned drill points, and/or the like. Additionally, the model may be validated by transmitting or otherwise providing the model generated in step 26 to the orthopaedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopaedic surgeon for validation.

After the model has been validated in process step 28, the customized patient-specific orthopaedic surgical instrument is fabricated in process step 30. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument. The fabricated customized patient-specific orthopaedic instrument is subsequently shipped or otherwise provided to the orthopaedic surgeon. The surgeon performs the orthopaedic surgical procedure in process step 32 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

Figure 10:
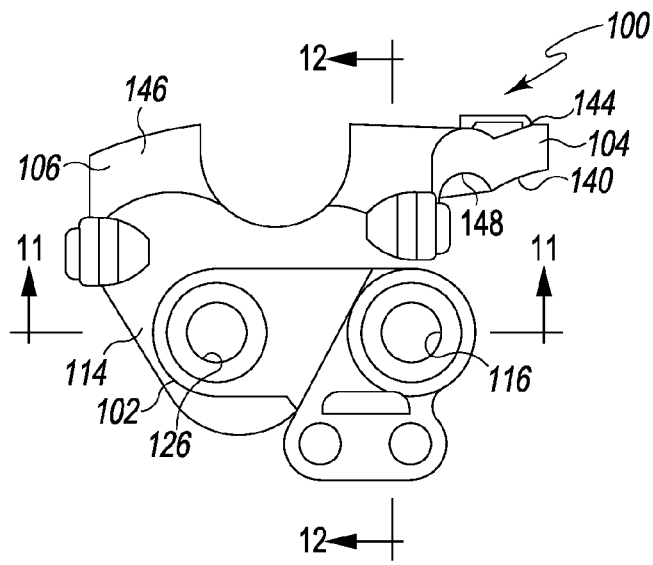
FIG. 10 is an anterior elevation view of a customized patient-specific tibial pin guide.
Figure 11:
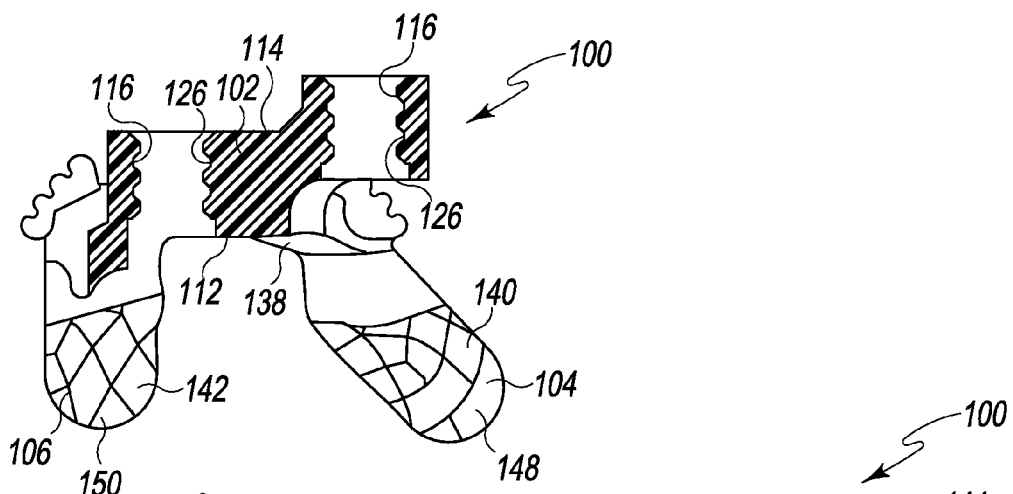
FIG. 11 is a cross section view of the customized patient-specific tibial pin guide taken along the line 11-11 of FIG. 10, as viewed in the direction of the arrows.
Figure 12:
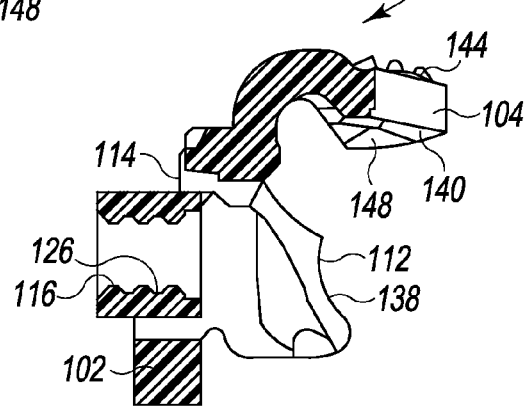
FIG. 12 is a cross section view of the customized patient-specific tibial pin guide taken along the line 12-12 of FIG. 10, as viewed in the direction of the arrows.

Referring now to FIGS. 10-12, in one embodiment, the customized patient-specific orthopaedic surgical instrument may be embodied as a tibial pin guide 100. The pin guide 100 is configured to be coupled to a tibia of a patient. As will be described below in greater detail, the tibial pin guide 100 is used to install a pair of guide pins 160 in a location on the tibia of the patient that has been customized for that particular patient. However, the tibial pin guide 100 is devoid of a cutting guide. As a result, once the tibial pin guide 100 has been used to install the guide pins 160, it is removed from the patient's tibia and a patient-universal cutting block 162 (see FIG. 20) is installed on the guide pins 160 and thereafter used to resect the patient's tibia. This is in contrast to the fabrication and use of a customized patient-specific cutting block. Such an arrangement allows for a certain degree of customization of the surgical procedure by customizing the placement of the guide pins 160 to the patient's anatomy, while also enjoying the cost benefits associated with the use of a reusable patient-universal cutting block.

The pin guide 100 includes a body 102 configured to be coupled to the anterior side of the patient's tibia and two arms or tabs 104, 106 which extend posteriorly away from the body 102. The tabs 104, 106 are configured to wrap around a proximal end of the tibia as discussed in more detail below. The pin guide 100 may be formed from any suitable material. For example, the pin guide 100 may be formed from a plastic or resin material. In one particular embodiment, the pin guide 100 is formed from Vero resin using a rapid prototype fabrication process. However, the pin guide 100 may be formed from other materials in other embodiments. For example, in another particular embodiment, the pin guide 100 is formed from a polyimide thermoplastic resin, such as a Ultem resin, which is commercially available from Saudi Basic Industries Corporation Innovative Plastics of Riyhadh, Saudi Arabia. In the illustrative embodiment described herein, the pin guide 100 is formed as a monolithic polymer structure.

The body 102 of the pin guide 100 includes a bone-contacting or bone-facing surface 112 and an outer surface 114 opposite the bone-facing surface 112. The body 102 has a number of guide holes 116 defined therethrough. A removable drill bushing 118 is locked into each guide hole 116. As will be described below in greater detail, the removable drill bushings 118 may be installed in the pin guide 100 for use in a surgical procedure and then removed from the pin guide 100 after the procedure. Whereas the pin guide 10 is customized component that is disposed of after its single use on the patient for which it was made, the removed drill bushings 118 may be sterilized and reused in a subsequent surgical procedure.

The bone-facing surface 112 of the pin guide's body 102 includes a negative contour 138 configured to receive a portion of the anterior side of the patient's tibia having a corresponding contour and, optionally, a portion of the medial side of the patient's tibia. The customized patient-specific negative contour 138 of the bone-contacting surface 112 allows the positioning of the pin guide 100 on the patient's tibia in a unique pre-determined location and orientation. In the exemplary embodiment described herein, the negative contour 138 is selected such that the pin guide 100 is configured to be coupled to the patient's tibia on an anterior surface of the tibia, although it may also be configured to be coupled to the anterior-medial side of the patient's tibia.

The tabs 104, 106 include a bone-contacting or bone-facing surface 140, 142, respectively, and an outer surface 144, 146, respectively, opposite the bone-facing surface 140, 142. The bone-facing surface 140 of the tab 104 includes a negative contour 148 configured to receive a portion of the proximal side of the patient's tibia having a respective corresponding contour. Similarly, the bone-facing surface 142 of the tab 106 includes a negative contour 150 configured to receive a portion of the proximal side of the patient's tibia having a respective corresponding contour.

As discussed above, the arms or tabs 104, 106 extend posteriorly from the body 102 to define a U-shaped opening therebetween. The tabs 104, 106 may extend from the body 102 the same distance or a different distance. Moreover, as shown in FIG. 11. the tabs 104, 106 may extend posteriorly at a non-parallel angle relative to one another.

In some embodiments, the negative contours 138, 148, 150 of the bone-contacting surfaces 112, 140, 142 of the customized patient-specific pin guide 100 may or may not match the corresponding contour surface of the patient's bone. That is, as discussed above, the negative contours 138, 148, 150 may be scaled or otherwise resized (e.g., enlarged) to compensate for the patient's cartilage or lack thereof.

As can be seen in FIGS. 13-15, the removable drill bushing 118 includes a head 120 that is contoured to be gripped by a surgeon's fingers. A post 122 extends away from the head 120 and includes a locking flange 124 formed on the outer surface thereof. The locking flange 124 is utilized to lock the post 122 within one of the guide holes 116 of the pin guide 100. Specifically, a locking slot 126 is formed in the pin guide's body 102 proximate to each of the guide holes 116. The locking slots 126 extend in a direction parallel to the axis of each of the respective guide holes 116 and open into the guide holes 116. In the illustrative embodiment of FIGS. 10-15, the locking flanges 124 of the removable drill bushings 118 are embodied as a number of male threads 124 extending helically around the outer surface of the post 122, with the locking slots 126 of the pin guide 100 being embodied as a number of female threads 126 extending helically around the periphery of each of the guide holes 116. The drill bushing's male threads 124 are sized to thread into the female threads 126 formed in the guide holes 116 of the pin guide 100.

An elongated bore 128 extends through the removable drill bushing 118. The bore 128 is sized to receive a drill such that the patient's tibia may be pre-drilled prior to installation of the guide pins 160. As shown in FIG. 15, each end of the bore 128 is countersunk. The countersunk opening on the drill bushing's head 120 functions as a lead-in to facilitation insertion of the drill and the guide pins 160 into the bore 128.

The removable drill bushings 118 may be provided to the surgeon separately from the pin guide 100. In particular, one or more of the removable drill bushings 118 may be provided to the surgeon in a separate sterile package from the sterile package that includes the pin guide 100. Unlike the pin guide 100 that is designed as a single-use disposable component, the removable drill bushings may be sterilized and reused after each procedure. As such, additional drill bushings 118 may not be needed each time a new pin guide 100 is procured by the surgeon.

The removable drill bushings 118 may be constructed from a medical-grade metal such as stainless steel, cobalt chrome, or titanium, although other metals or alloys may be used.

As shown in FIGS. 16-20, a surgeon may use the customized patient-specific tibial pin guide 100 to install a pair of guide pins 160 in locations on the tibia of the patient that have been customized for that particular patient. A patient-universal cutting block 162 may then be installed on the custom-located guide pins 160 and thereafter used to resect the patient's tibia. Such an arrangement allows for a certain degree of customization of the surgical procedure by customizing the placement of the guide pins 160 to the patient's anatomy, while also enjoying the cost benefits associated with use of the reusable patient-universal cutting block 162.

Figure 16:
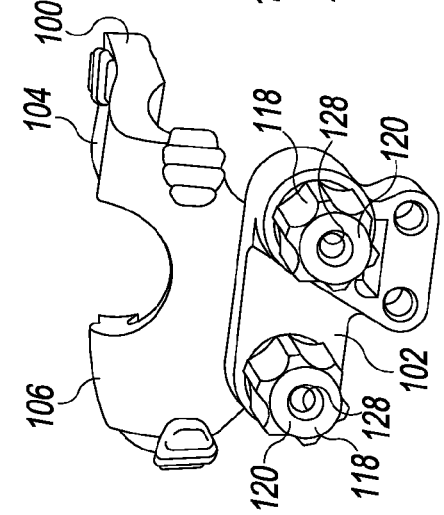

As shown in FIG. 16, the surgical procedure commences with assembly of the customized patient-specific surgical instrument on a prep table or other part of the surgery room. To do so, the surgeon first obtains a customized patient-specific pin guide 100 that was fabricated for the particular patient being treated by the surgeon. The pin guide 100 is fabricated in the manner described above in regard to FIGS. 1-9. Once the customized patient-specific pin guide 100 has been obtained, the surgeon then takes a pair of the sterilized removable drill bushings 118 and installs them to the pin guide 100. In particular, the surgeon obtains a pair of the removable drill bushings 118 from a previous procedure (after being sterilized) or new drill bushings 118 (from the manufacturer's sterilized packaging). Thereafter, the surgeon inserts the threaded post 122 of one of the drill bushings 118 into one of the guide holes 116 formed in the pin guide 100 and rotates the head 120 of the drill bushing 118 so that the external threads 124 formed on the outer surface of the post 122 are threaded into the female threads 126 formed in the guide hole 116. The surgeon then obtains the other drill bushing 118 and installs it in the pin guide's other guide hole 116 in a similar manner.

Figure 17:
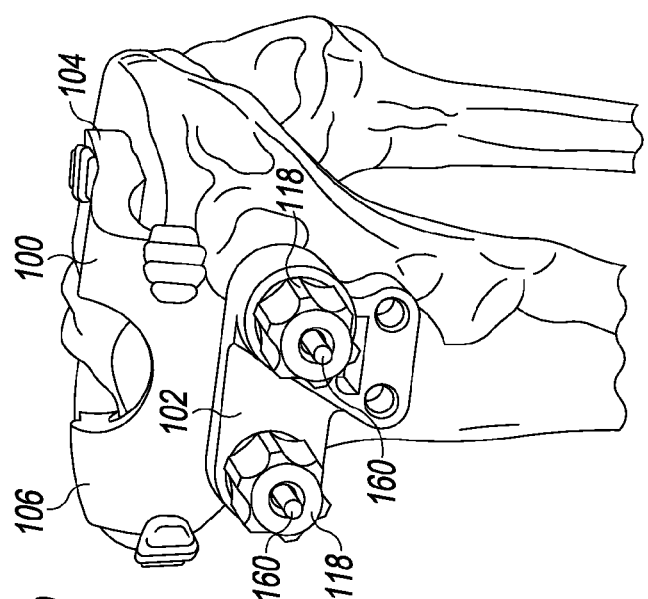

As shown in FIG. 17, the assembled customized patient-specific pin guide 100 is then coupled to the proximal end of the patient's tibia. Because the bone-contacting surfaces 112, 140, 142 of the pin guide 100 include the negative contours 138, 148, 150, the pin guide 100 is coupled to the patient's tibia in a pre-planned, unique position. When so coupled, the tabs 104, 106 wrap around the proximal end of the patient's tibia, and the elongated bores 128 of the drill bushings 118 extend in the anterior/posterior direction away from the anterior surface of the patient's tibia.

The surgeon then installs the guide pins 160. To do so, the surgeon first drills pilot holes in the patient's tibia by advancing a drill (not shown) through the guide bore 128 of each of the drill bushings 118. The surgeon then inserts a guide pin 160 through the guide bore 128 of each of the drill bushings 118 and into the drilled pilot holes. As such, the guide pins 160 are installed in the patient's tibia in customized, patient-specific locations created by use of the customized, patient-specific pin guide 100. It should be appreciated that if the guide pins 160 are self-tapping pins, pre-drilling of the patient's tibia is not necessary.

Figure 18:
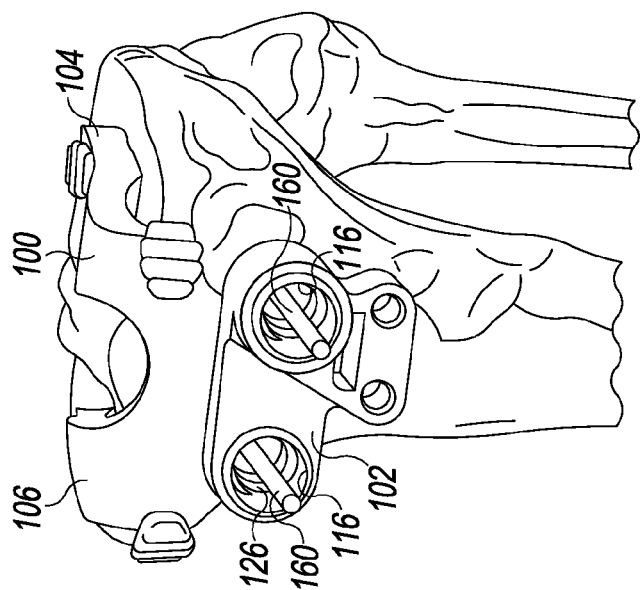
FIGS. 16-20 show the customized patient-specific tibial pin guide of FIG. 10 being used to surgically resect the tibia of a patient.

As shown in FIG. 18, once the guide pins 160 are installed in the patient's tibia in the customized, patient-specific locations by use of the pin guide 100, the drill bushings 118 are removed. Specifically, the surgeon first grips the head 120 of one of the drill bushings 118 and rotates it in the opposite direction it was rotated during installation (e.g., counterclockwise) such that the external threads 124 formed on the outer surface of the drill bushing's post 122 are unthreaded from the female threads 126 formed in the guide hole 116. Once unthreaded, the drill bushing 118 may be lifted away from the pin guide 100. The surgeon then removes the other drill bushing 118 from the pin guide's other guide hole 116 in a similar manner. The drill bushings 118 are not disposed of, but rather may be retained and sterilized for use in a subsequent surgical procedure in combination with a customized patient-specific pin guide 100 that has been fabricated for another patient.

Figure 20:
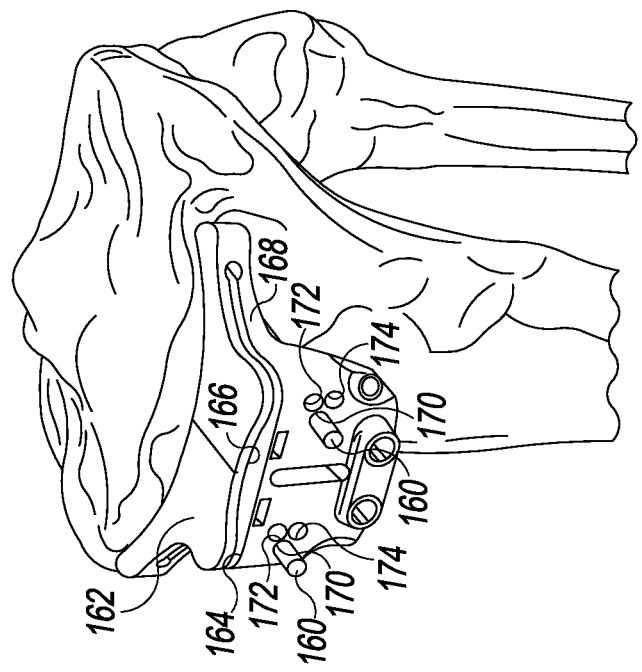
Figure 19:
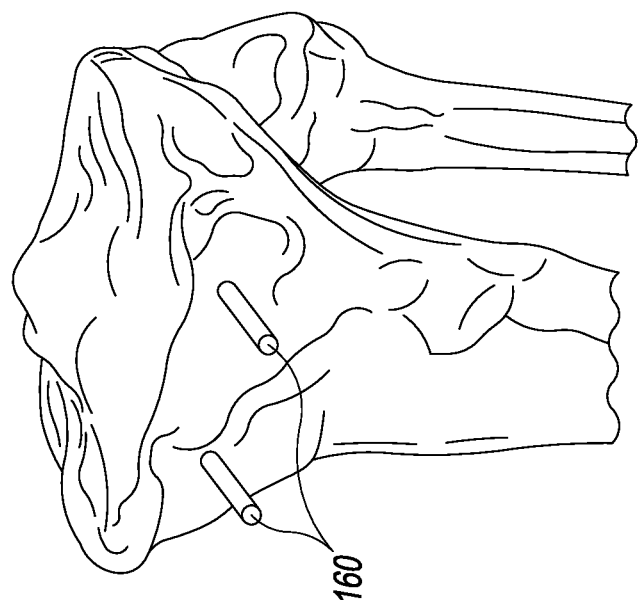

As shown in FIG. 19, with the drill bushings 118 removed, the pin guide 100 is then de-coupled and removed from the patient's tibia. In doing so, the guide pins 160 are left behind in the patient's tibia in the customized, patient-specific locations created by use of the pin guide 100. As shown in FIG. 20, the patient-universal cutting block 162 is then used to resect the patient's tibia in the desired location and orientation. The patient-universal cutting block 162 includes a cutting guide 164 that, in the illustrative embodiment described herein, is in the form of a cutting slot 166 formed in the cutting block's body 168. The body 168 of the patient-universal cutting block 162 also has multiple pairs of guide pin holes formed therein. For example, in the illustrative embodiment described herein, the cutting block's body 168 has three different corresponding pairs of guide pin holes 170, 172, and 174. As will be described below in greater detail, the patient-universal cutting block 162 may be selectively positioned on the guide pins 160 by use of the guide pin holes 170, 172, and 174 to alter the position of the cutting slot 166 and hence the amount of bone removed during resection. For example, in FIG. 20, the cutting block is positioned in the pair of guide pin holes 170 corresponding to the baseline or "zero" setting. If the surgeon desires to take off more bone (e.g., +2 mm) than would otherwise be removed by use of the zero setting, the surgeon can remove the patient-universal cutting block 162 from the guide pins 160 and reinstall it such that the guide pins 160 are received into the guide pin holes 172. Conversely, if the surgeon desires to take off less bone (e.g., −2 mm) than would otherwise be removed by use of the zero setting, the surgeon can remove the patient-universal cutting block 162 from the guide pins 160 and reinstall it such that the guide pins 160 are received into the guide pin holes 174.

As shown in FIG. 20, once the patient-universal cutting block 162 has been installed with use of the desired pair of guide pin holes (in the illustrative example of FIG. 20, the guide pin holes 170), the surgeon may use the patient-universal cutting block to resect the proximal end of the patient's tibia. To do so, the surgeon advances a bone saw blade into the cutting slot 166 and cuts the tibia. If need be, the surgeon may then reposition the cutting block 162 with use of a different pair of guide pin holes to perform a second cut to remove more bone. Once the patient's proximal tibia has been resected, the surgeon may then continue with the surgical procedure.

Referring now to FIGS. 21-23, the customized patient-specific instruments described herein may also be embodied as a customize patient-specific femoral pin guide 200. The pin guide 200 is configured to be coupled to the femur of a patient. The pin guide 200 includes a body 202 configured to be coupled to the anterior side of the patient's femur and two arms or tabs 204, 206, which extend posteriorly away from the body 202. The tabs 204, 206 are configured to wrap around a distal end of the femur. Each of the tabs 204, 206 includes an inwardly-curving or otherwise superiorly extending lip 208, 210.

Like the tibial pin guide 100, the femoral pin guide 200 may be formed from a material such as a plastic or resin material. In some embodiments, the pin guide 200 may be formed from a photo-curable or laser-curable resin. In one particular embodiment, the pin guide 200 is formed from a Vero resin using a rapid prototype fabrication process. However, the pin guide 200 may be formed from other materials in other embodiments. For example, in another particular embodiment, the pin guide 200 is formed from a polyimide thermoplastic resin, such as a Ultem resin. In the illustrative embodiment described herein, the pin guide 200 is embodied as a monolithic structure.

The body 202 includes a bone-contacting or bone-facing surface 212 and an outer surface 214 opposite the bone-facing surface 212. The body 202 has a number of threaded guide holes 216 defined therethrough. One of the removable drill bushings 118 may be threaded into each of the guide holes 216. In addition to the guide holes 216 formed in the pin guide's body 202, another pair of guide holes 216 is formed in the tabs 204, 206. Similarly to as described above in regard to the tibial pin guide 100, the removable drill bushings 118 may be installed in the femoral pin guide 200 for use in a surgical procedure and then removed from the pin guide 200 after the procedure. Like the tibial pin guide 100, the femoral pin guide 200 is a customized component that is disposed of after its single use on the patient for which it was made.

The bone-facing surface 212 of the femoral pin guide's body 202 includes a negative contour 228 configured to receive a portion of the anterior side of the patient's femur having a corresponding contour. As discussed above, the customized patient-specific negative contour 228 of the bone-contacting surface 212 allows the positioning of the pin guide 200 on the patient's femur in a unique pre-determined location and orientation.

As alluded to above, the arms or tabs 204, 206 extend posteriorly from the body 202 to define a somewhat U-shaped opening therebetween. The tabs 204, 206 may extend from the body 202 the same distance or a different distance. Each of the tabs 204, 206 has a threaded guide hole 216 formed therein. One of the removable drill bushings 118 may be threaded into each guide hole 216 of the tabs 204, 206. In particular, the guide holes 216 of the tabs 204, 206 have a similar diameter and configuration as the guide holes 216 of the pin guide's body 202 and the guide holes 116 of the tibial pin guide 100. As such, the removable drill bushings 118 are interchangeable between the tibial pin guide 100 and the femoral pin guide 200.

The tabs 204, 206 include a bone-contacting or bone-facing surface 240, 242, respectively, and an outer surface 244, 246, respectively, opposite the bone-facing surface 240, 242. The bone-facing surface 240 of the tab 204 includes a negative contour 248 configured to receive a portion of the distal side of the patient's femur having a respective corresponding contour. Similarly, the bone-facing surface 242 of the tab 206 includes a negative contour 250 configured to receive a portion of the distal side of the patient's femur having a respective corresponding contour.

In some embodiments, the negative contours 228, 248, 250 of the bone-contacting surfaces 212, 240, 242 of the customized patient-specific pin guide 200 may or may not match the corresponding contour surface of the patient's bone. That is, as discussed above, the negative contours 228, 248, 250 may be scaled or otherwise resized (e.g., enlarged) to compensate for the patient's cartilage or lack thereof.

As shown in FIG. 23, the femoral pin guide 200 may be coupled to the distal end of the patient's femur. Because the bone-contacting surfaces 212, 240, and 242 of the pin guide 200 include the negative contours 228, 248, 250, the femoral pin guide may be coupled to the patient's femur in a pre-planned, unique position. When so coupled, the tabs 204, 206 wrap around the distal end of the patient's femur. Additionally, when the femoral pin guide 200 is coupled to the patient's femur, a portion of the anterior side of the femur is received in the negative contour 228 of the body 202 and a portion of the distal side of the patient's femur is received in the negative contours 248, 250 of the tabs 204, 206, respectively.

Once coupled to the patient's distal femur, a surgeon may use the customized patient-specific femoral pin guide 200 to install two pairs of guide pins 160 in locations that have been customized for that particular patient. One pair of the guide pins 160 is installed in a custom patient-specific location on the anterior side of the patient's femur. The other pair of guide pins 160 is installed on the distal side of the patient's femur. With the pin guide 200 removed, a patient-universal cutting block or blocks (not shown) may then be installed on the custom-located guide pins 160 and thereafter used to resect the patient's femur. Such an arrangement allows for a certain degree of customization of the surgical procedure by customizing the placement of the guide pins 160 to the patient's anatomy, while also enjoying the cost benefits associated with the use of a reusable patient-universal cutting block(s).

Referring now to FIGS. 24-27, there is shown another embodiment of the pin guide 100 and the removable drill bushing 118. The pin guide 100 and the drill bushing 118 shown in FIGS. 24-27 are essentially the same as the pin guide 100 and the drill bushing 118 shown in FIGS. 10-20 with the exception of the locking mechanism that locks the removable drill bushing 118 within the guide holes 116 of the pin guide 100. In particular, in lieu of locking threads, in the illustrative embodiment of the pin guide 100 and the removable drill bushing 118 shown in FIGS. 24-27 utilizes a cam lock arrangement.

Figure 24:
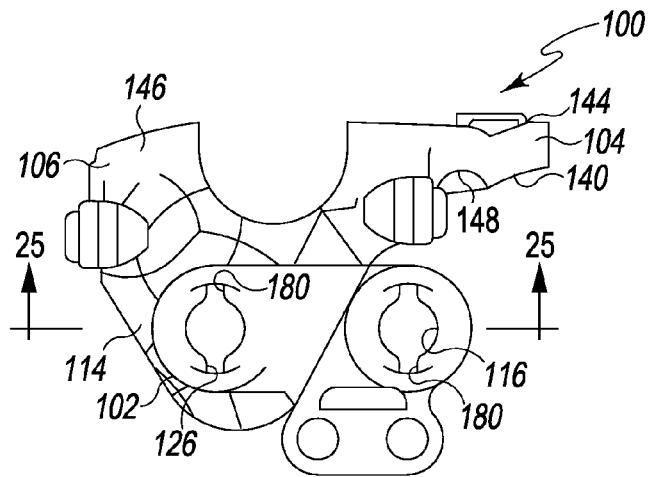
FIG. 24 is an anterior elevation view of another embodiment of a customized patient-specific tibial pin guide.
Figure 25:
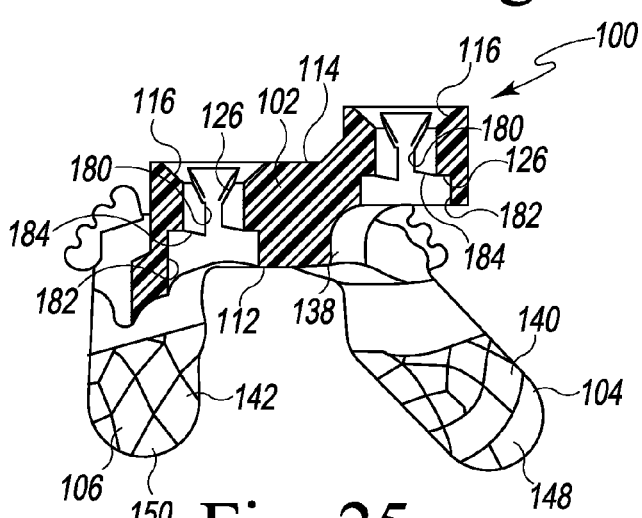
FIG. 25 is a cross section view of the customized patient-specific tibial pin guide taken along the line 25-25 of FIG. 24, as viewed in the direction of the arrows.

As shown in FIGS. 24 and 25, the locking slot 126 formed in the pin guide's body 102 proximate to each of the guide holes 116 is not helical, but rather includes two elongated channels 180 positioned on opposite sides of the guide hole 116 and an annular recess 182 formed within the pin guide's body 102. The outer ends of the channels 118 open to the outer surface 114 of the guide pin's body 102, with the inner ends of the channels 180 opening into the annular recess 182. As can be seen in the cross sectional view of FIG. 25, a shoulder 184 defines the anterior side of the locking slot's annular recess 182. As can also be seen in FIG. 25, the shoulder 184 is embodied as an angled cam surface. As will be described below, the locking flange 124 of the removable drill busing engages the cam surface to lock the removable drill bushing 118 to the pin guide 100.

Figure 26:
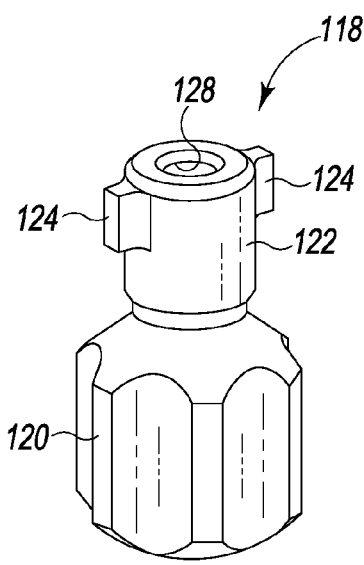
FIG. 26 is a perspective view of another embodiment of a removable drill bushing.
Figure 27:
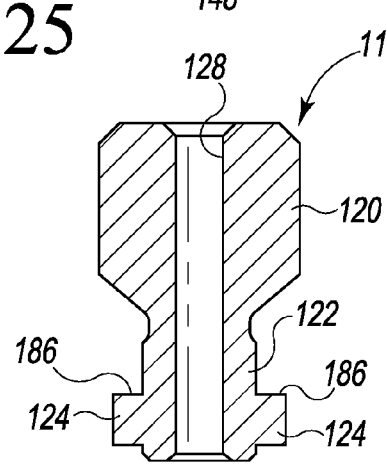
FIG. 27 is a cross section view of the removable drill bushing of FIG. 26.

The locking flange 124 of the removable drill bushing 118 of FIGS. 26 and 27 is embodied as a pair of tabs extending outwardly from opposite sides of its post 122. The tabs 124 are sized and positioned to be received into the respective channels 180 of the pin guide's locking slot 126. Specifically, to lock the removable drill bushing 118 to the pin guide 100, each of the tabs 124 is first aligned with one of the channels 180 and thereafter advanced into the channels 180. When the tabs 124 have been advanced into the channels 180 far enough to clear the shoulder 184, the head 120 of the removable drill bushing 118 may be rotated approximately 90° thereby also rotating the tabs 124. Such rotation of the tabs 124 removes the tabs from alignment with the channels 180 thereby capturing the tabs 124 within the annular recess 182. Such rotation also causes the anterior cam surface 186 of the tabs 124 to engage the cam surface of the shoulder 184. This cam locks the removable drill bushing 118 to the drill guide 100.

To unlock the removable drill bushing 118 from the drill guide 100, the head 120 of the removable drill bushing 118 may be rotated in the opposite direction it was rotated during installation to a position in which the tabs 124 are aligned with the channels 180. Once the tabs 124 are aligned in such a manner, the post 122 of the removable drill bushing 118 may be slid out of the guide hole 116 thereby disassembling the removable drill bushing 118 from the pin guide 100.

It should be appreciated that although the locking mechanism of FIGS. 24-27 is illustratively described within the context of the tibial pin guide 100, the femoral pin guide 200 may also be modified to include such a cam lock arrangement in lieu of the threaded arrangement described above in regard to FIGS. 21-23.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

What is claimed is:

1. A method of performing an orthopaedic surgical procedure on a bone of a patient, comprising:
   assembling a customized patient-specific pin guide assembly by (i) locking a first removable drill bushing into a first hole of a customized patient-specific pin guide, and (ii) locking a second removable drill bushing into a second hole of the customized patient-specific pin guide,
   positioning the assembled customized patient-specific pin guide assembly in contact with the bone of the patient,
   inserting a pair of guide pins into the bone of the patient by (i) advancing a first guide pin of the pair of guide pins through the first removable drill bushing, and (ii) advancing a second guide pin of the pair of guide pins through the second removable drill bushing,
   removing the customized patient-specific pin guide assembly from the bone of the patient without removing the pair of guide pins from the bone of the patient,
   positioning a patient-universal cutting block into contact with the bone of the patient such that the pair of guide pins is received into a pair of guide pin holes defined in the patient-universal cutting block, and
   making a cut in the bone of the patient with the patient-universal cutting block.

2. The method of claim 1, wherein removing the customized patient-specific pin guide assembly from the bone of the patient comprises:
   disassembling the customized patient-specific pin guide assembly by (i) unlocking the first removable drill bushing from the first hole of the customized patient-specific pin guide, and (ii) unlocking the second removable drill bushing from the second hole of the customized patient-specific pin guide, and
   removing the disassembled customized patient-specific pin guide assembly from the bone of the patient without removing the pair of guide pins from the bone of the patient.

3. The method of claim 1, further comprising:
   removing the patient-universal cutting block from the bone of the patient prior to making the cut in the bone of the patient, and
   repositioning the patient-universal cutting block into contact with the bone of the patient such that the pair of guide pins is received into a second, different pair of guide pin holes defined in the patient-universal cutting block prior to making the cut in the bone of the patient.

4. The method of claim 3, wherein repositioning the patient-universal cutting block into contact with the bone of the patient comprises:
   determining an amount of bone to be removed from the bone of the patient subsequent to positioning the patient-universal cutting block into contact with the bone of the patient,
   selecting the pair of second, different guide pin holes which corresponds to the amount of bone to be removed from the bone of the patient from a plurality of pairs of guide pin holes, and
   repositioning the patient-universal cutting block into contact with the bone of the patient such that the pair of guide pins is received into the selected second, different pair of guide pin holes defined in the patient-universal cutting block prior to making the cut in the bone of the patient.

5. The method of claim 1, wherein:
   positioning the assembled customized patient-specific pin guide assembly in contact with the bone of the patient comprises positioning the assembled customized patient-specific pin guide assembly in contact with a femur of the patient, and
   making the cut in the bone of the patient with the patient-universal cutting block comprises making the cut in the femur of the patient with the patient-universal cutting block.

6. The method of claim 1, wherein:
   positioning the assembled customized patient-specific pin guide assembly in contact with the bone of the patient comprises positioning the assembled customized patient-specific pin guide assembly in contact with a tibia of the patient, and making the cut in the bone of the patient with the patient-universal cutting block comprises making the cut in the tibia of the patient with the patient-universal cutting block.

* * * * *